United States Patent [19]
Taylor

[11] Patent Number: 6,155,120
[45] Date of Patent: Dec. 5, 2000

[54] PIEZORESISTIVE FOOT PRESSURE MEASUREMENT METHOD AND APPARATUS

[76] Inventor: Geoffrey L. Taylor, 211 Oak Street, Winnipeg, Manitoba, Canada, R3M 3P7

[21] Appl. No.: 09/068,797
[22] PCT Filed: Nov. 14, 1996
[86] PCT No.: PCT/IB96/01467
§ 371 Date: May 13, 1998
§ 102(e) Date: May 13, 1998
[87] PCT Pub. No.: WO97/18450
PCT Pub. Date: May 22, 1997
[51] Int. Cl.[7] ................................... G01L 3/00
[52] U.S. Cl. ........................... 73/862.046; 73/865.7
[58] Field of Search .................. 73/862.046, 862.68, 73/862.044, 865.7

[56] References Cited

U.S. PATENT DOCUMENTS

| | | | |
|---|---|---|---|
| 4,739,211 | 4/1988 | Strachan | 310/321 |
| 4,754,930 | 7/1988 | Gorgen | 242/118.61 |
| 5,079,949 | 1/1992 | Tamori | 73/172 |
| 5,503,029 | 4/1996 | Tamori | 73/862.046 |
| 5,515,738 | 5/1996 | Tamori | 73/862.46 |
| 5,571,973 | 11/1996 | Taylot | 73/862.046 |

*Primary Examiner*—Max Noori
*Attorney, Agent, or Firm*—William L. Chapin

[57] ABSTRACT

A method and apparatus (68, 40) for measuring pressures exerted on 6 human feet or horses' hooves comprises a rectangular array of piezoresistive force sensors encapsulated in a thin polymer package (40) that is inserted into a shoe, or incorporated into a sock that may be pulled over a foot or hoof. The preferred embodiment employs novel piezoresistive normal force or pressure sensing elements (36) which include a polymer fabric mesh impregnated with conductive particles suspended in an elastomeric vehicle, preferably silicone rubber. The piezoresistive mesh layer (33) is sandwiched between an array of row (34) and column (31) conductor strip laminations, preferably made of a nylon mesh impregnated with printed metallic paths. In a variation (100) of the basic embodiment, each normal force sensor element (30) is bordered by laterally and longitudinally disposed pairs (80) of shear force sensor elements, each of the latter comprising a pair of adjacent resilient piezoresistive pads (83) that have longitudinally contacting lateral surfaces. The pads are slidably movable, and when urged into more or less intimate contact in response to shear forces directed normal to their tangent contact plane, the electrical resistance between the pads varies in a predetermined way as a function of the shear forces.

31 Claims, 33 Drawing Sheets

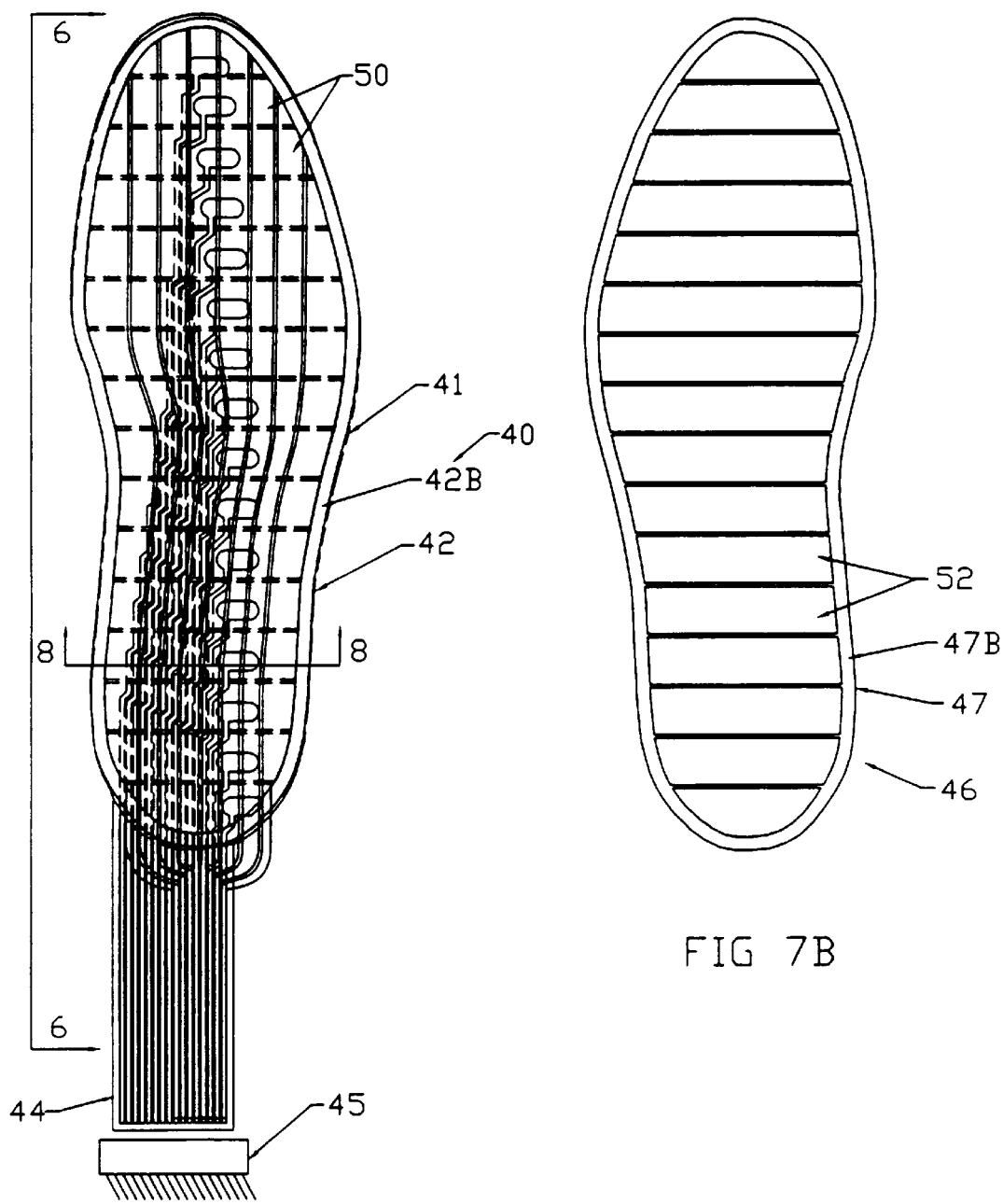

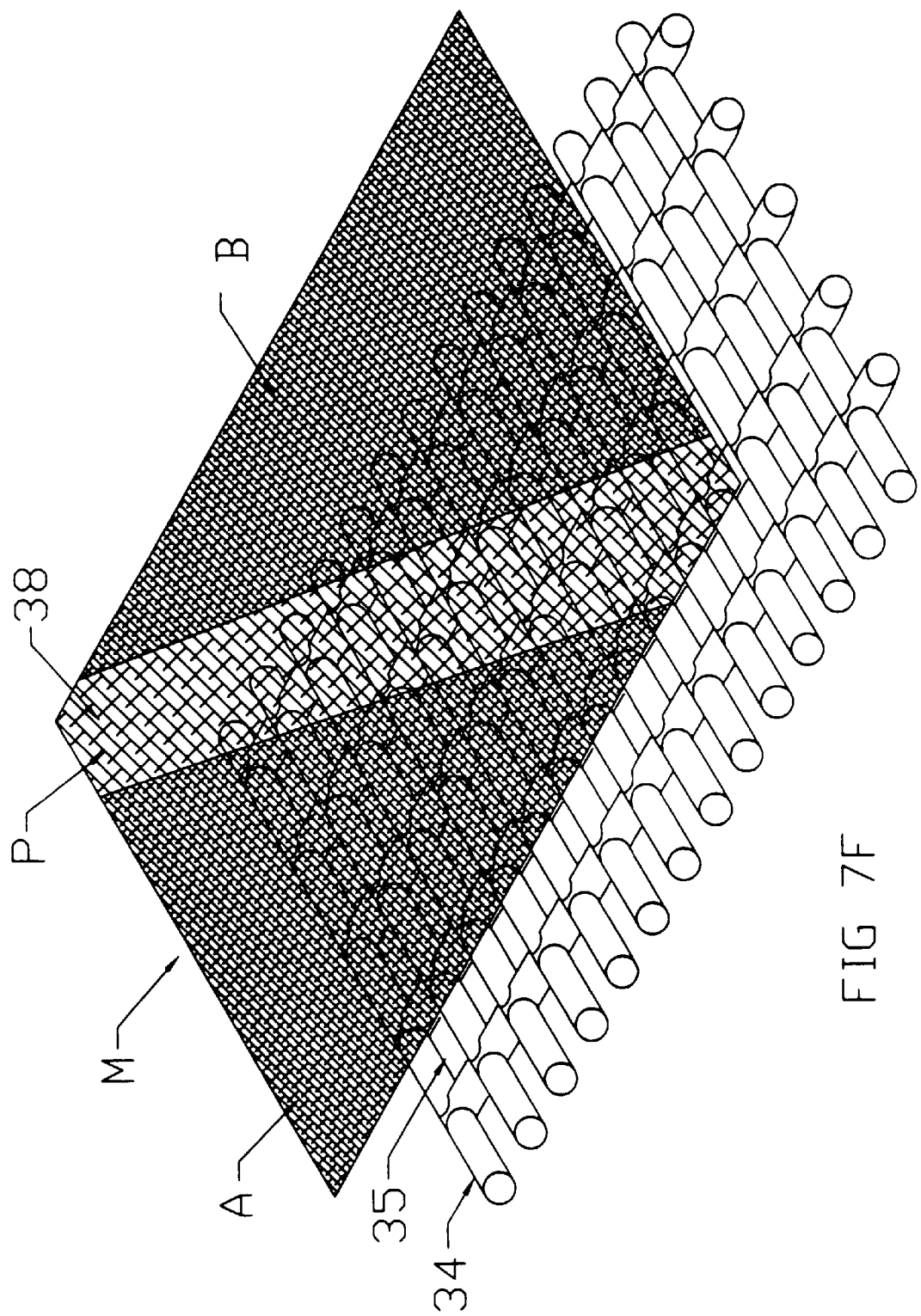

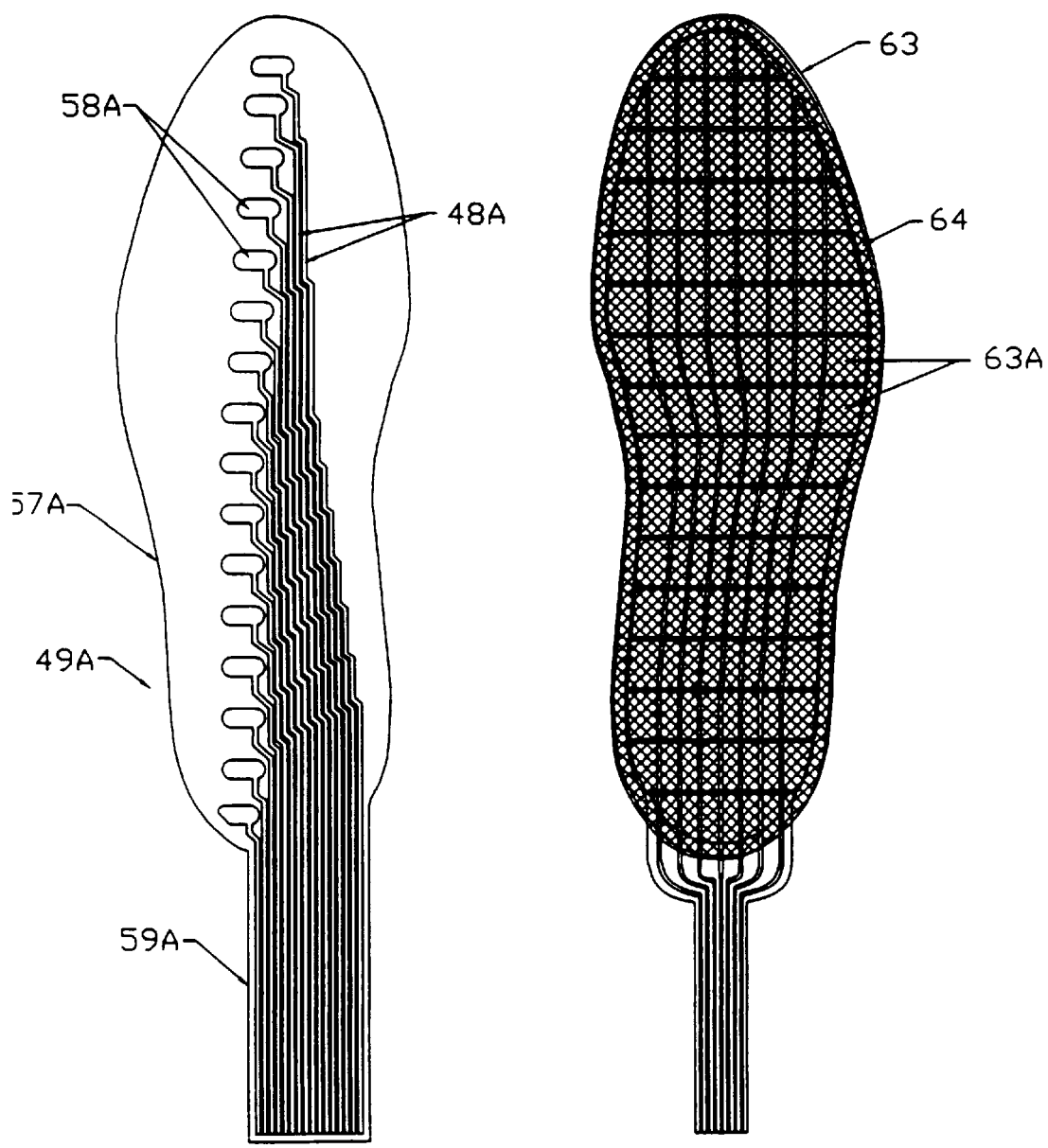

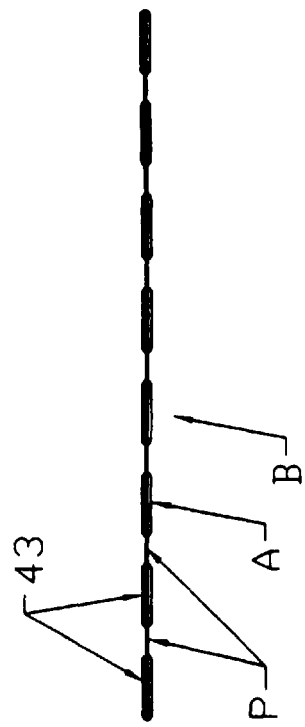
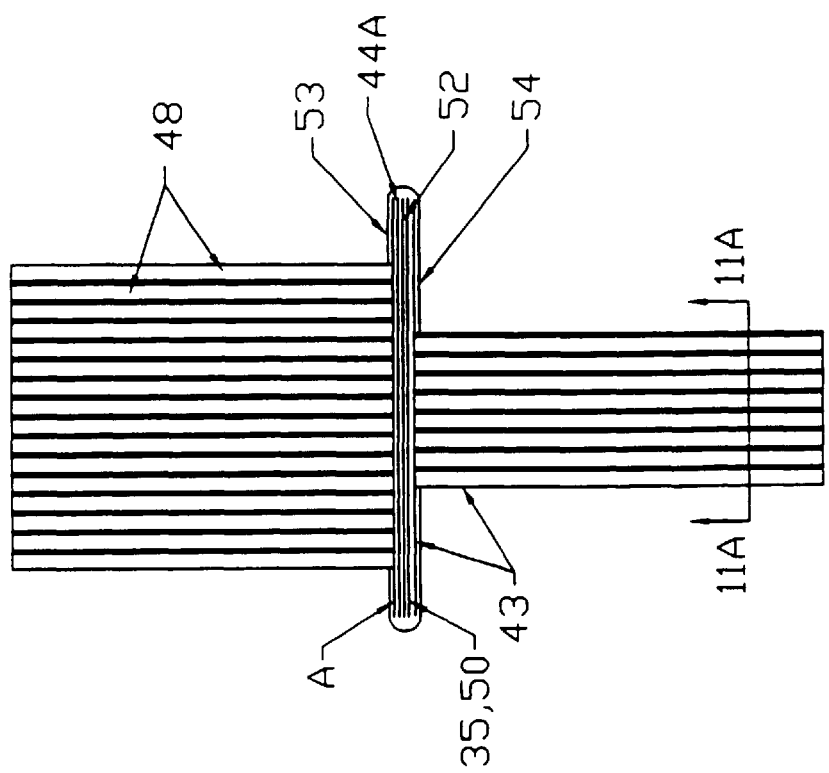

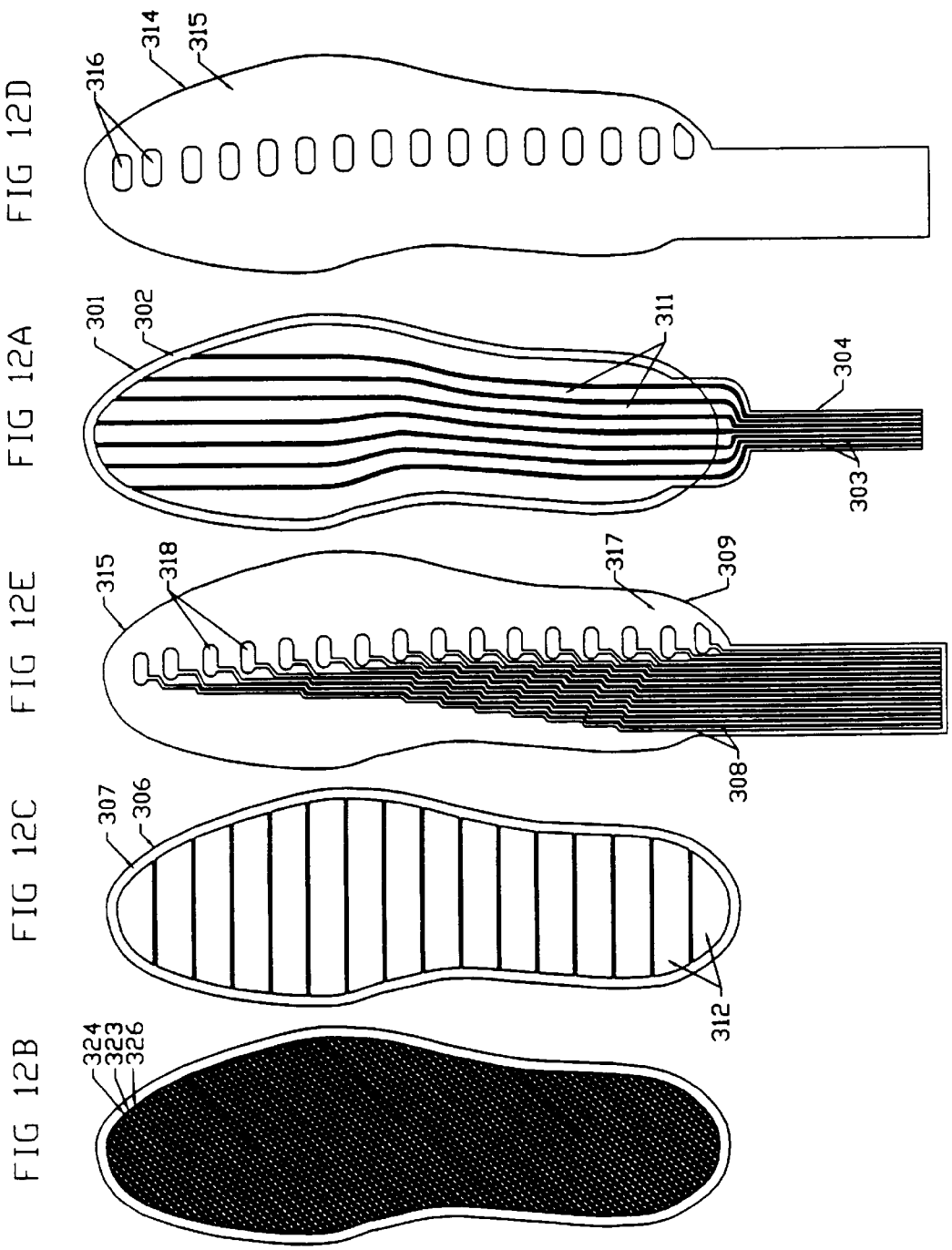

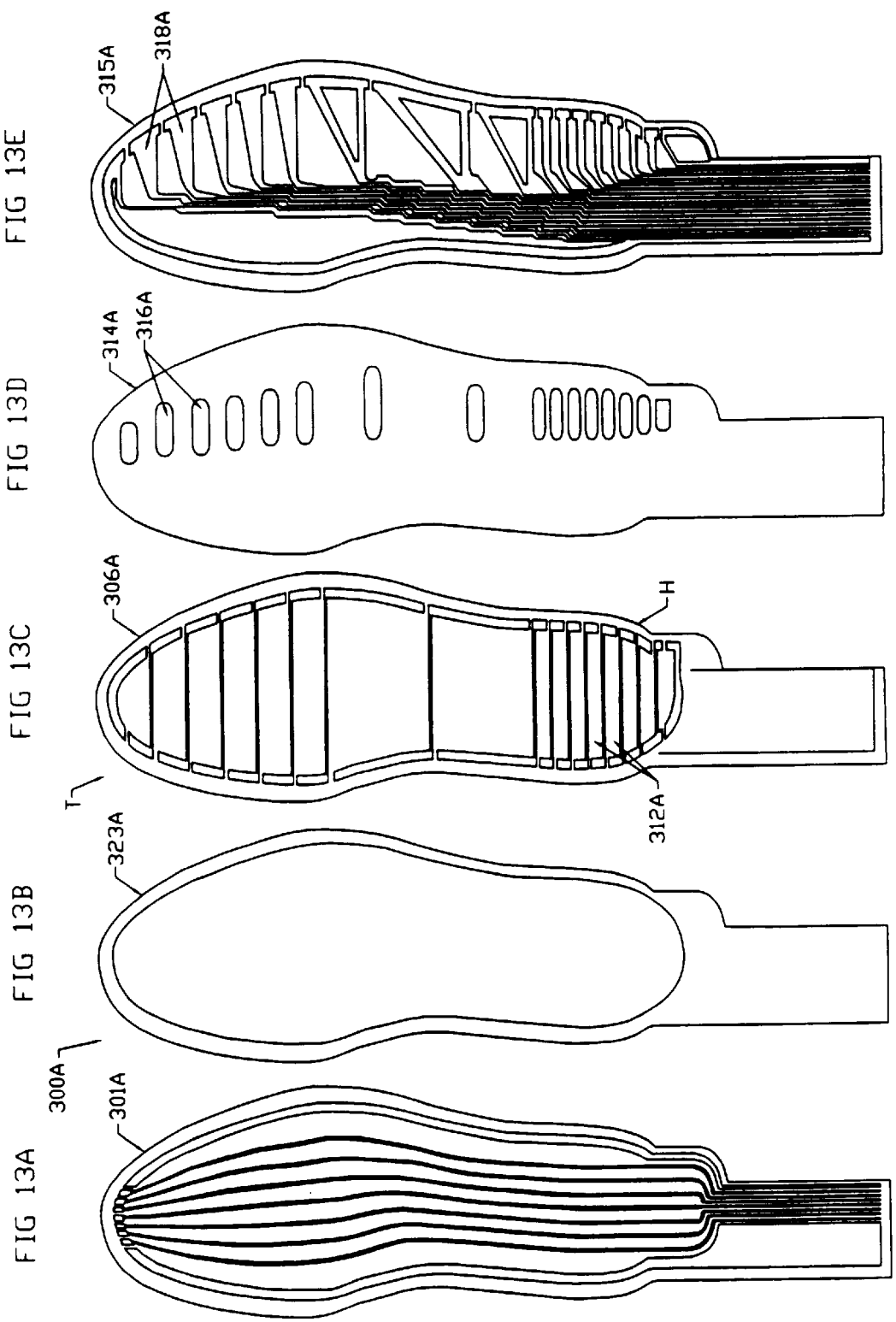

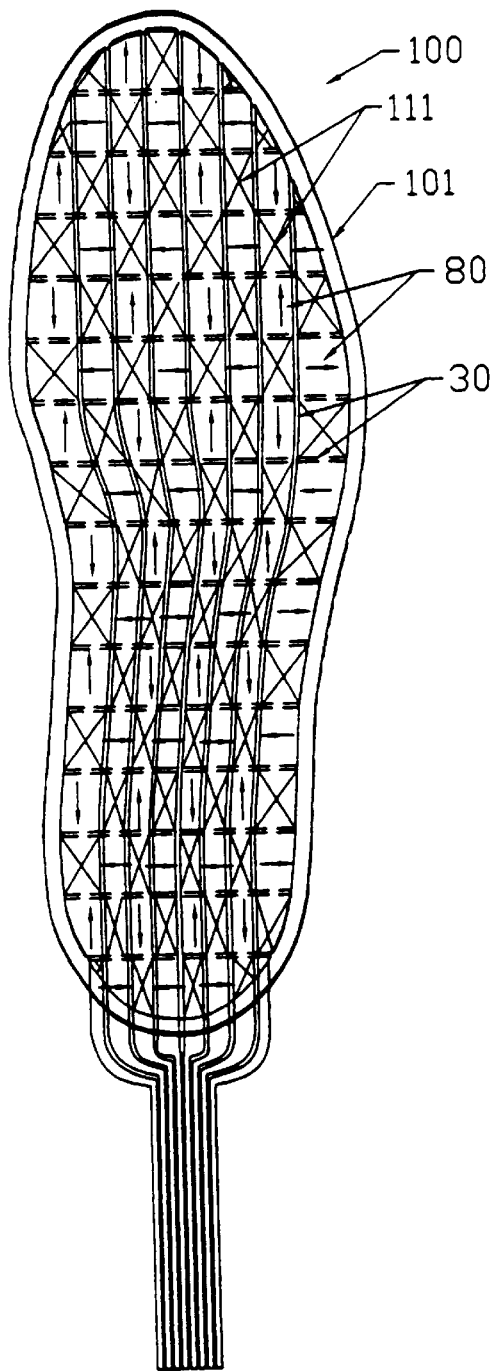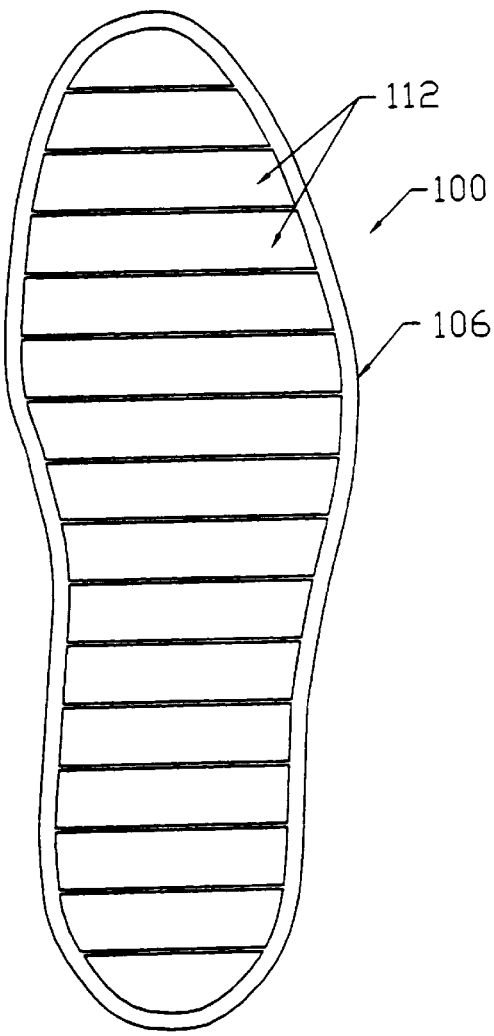
FIG 20D
FIG 20E

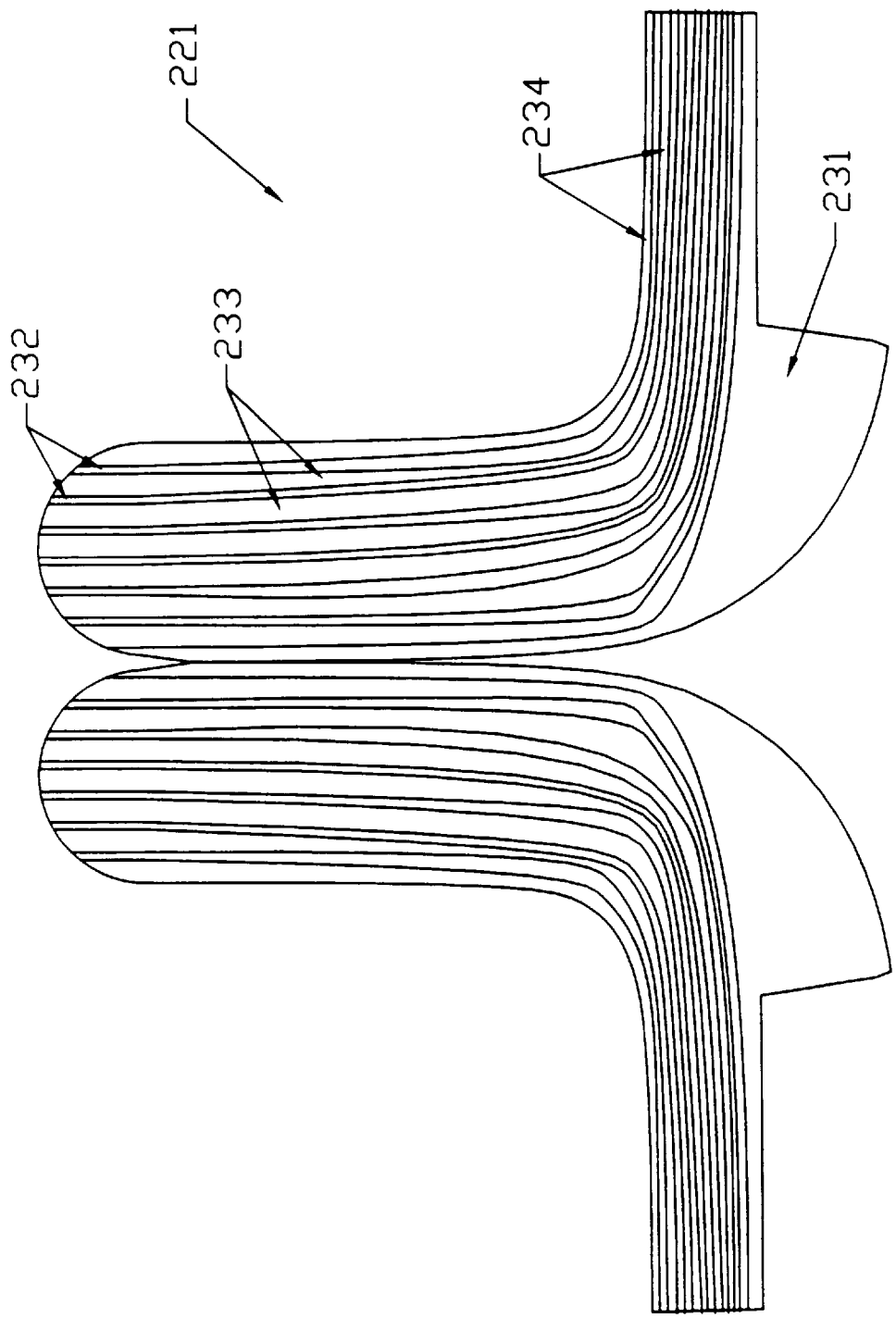

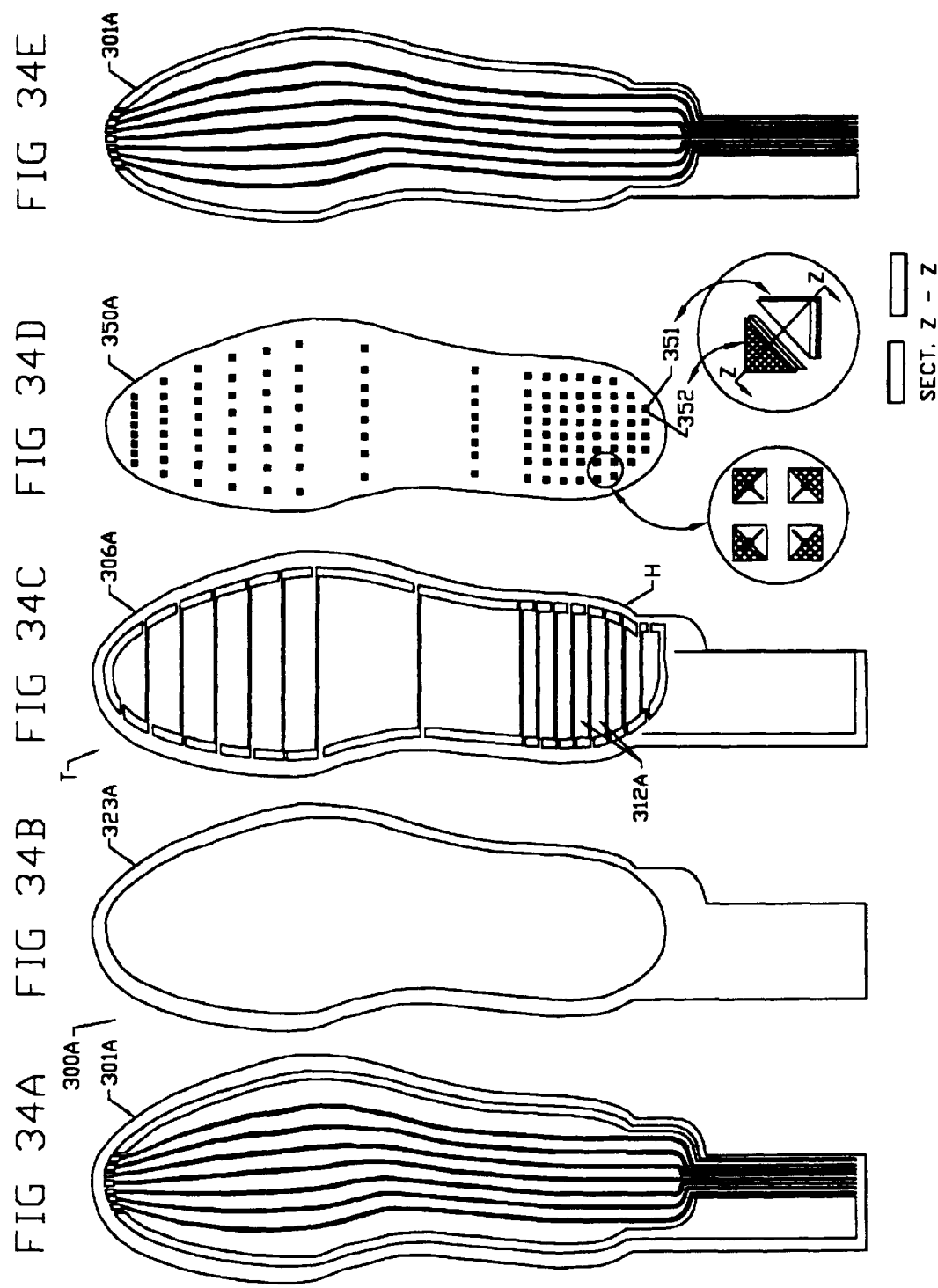

PIEZORESISTIVE FOOT PRESSURE MEASUREMENT METHOD AND APPARATUS

BACKGROUND OF THE INVENTION

A. Field of the Invention

The present invention relates to methods and apparatus for measuring pressures exerted on the feet of standing humans or animals such as horses. More particularly, the invention relates to a method and apparatus for providing a two-dimensional map of pressures exerted on the bottom of a human foot by a shoe, for example, or on the hoof of an animal, particularly, a horse.

B. Description of Background Art

People who must be on their feet for long periods of time, whether standing or walking, are well aware of the discomfort and fatigue that may be brought on by reaction pressures exerted on the bottoms of the feet by the ground or other surface supporting the weight of the person. Accordingly, substantial efforts have been exerted by manufacturers of shoes, ski boots and other footwear, in an effort to more uniformly distribute the pressures exerted by footwear on the feet of the wearer. In conjunction with these efforts, a variety of devices for measuring the forces applied to the foot by footwear have been disclosed in the following United States patents:

Levin et al., U.S. Pat. No. 4,121,453, Oct. 24, 1978, Foot Force Transducer, which discloses an apparatus for measuring foot forces during walking that uses a specially configured spring seated in a transducer plate to transmit static and dynamic forces on the foot during walking to strain gauges mounted on the transducer plate, which in turn, may be monitored and recorded for diagnostic purposes, particularly to aid in treating patients with lower extremities dysfunction.

Confer, U.S. Pat. No. 4,745,930, May 24, 1988, Force Sensing Insole For Electro-Goniometer, which discloses a force sensing insole that is adapted to be used in association with an electro-goniometer for analyzing the gait of a patient. The insole includes a body member composed of three overlying sheets of thin plastic material which are bonded together, with the intermediate sheet having cut-outs in each of the heel, ball and tow portions so as to define three separate internal chambers. A contact switch is positioned in each of the open chambers, and which comprises a plurality of parallel fingers formed of conductive ink on the inwardly facing surface of one of the outer sheets, and an area of conductive material on the inwardly facing surface of the outer sheet. The body member includes a laterally extending flexible strip, and which is adapted to flex and extend outwardly from the wearer's shoe. Also, lines of conductive ink are provided in the body member which extend from each of the contact switches to a terminal positioned at the end of the strip. In the preferred embodiment, switch closures are input to a radio frequency transmitter strapped to the waist of a subject, a remote receiver being used to monitor switch closures.

Franks, U.S. Pat. No. 4,858,621, Aug. 22, 1989, Foot Pressure Measurement System, which discloses a foot pressure measurement system in which pressure measurements are obtained from the variation of light output from an illuminated glass or transparent plate. A reflective material on the top surface of the plate causes an increase in light intensity escaping from the plate when pressure is applied to the reflective material. The accuracy and resolution of the pressure measurements are improved by obtaining a reference measurement of the background light intensity and distribution before pressure is applied and subsequently subtracting this background light from the light patterns produced when pressure is applied. The reflectance characteristics of the system are improved by using a photographic paper as the reflective material.

Seitz, U.S. Pat. No. 4,862,743, Sep. 5, 1989, Device For Measuring The Areal Distribution of Compressive Forces, which discloses a device for measuring the areal distribution of compressive forces which act substantially vertically with respect to a deformable measuring surface. A matrix arrangement of force sensors is provided, each of which is formed as a capacitance at crossings of substantially perpendicular conductor paths. The conductor paths are fixed on the opposed surfaces of an elastically deformable area-type dielectric and adapted to be connected by conductive elements to evaluator electronics. The conductor paths are printed on plastic substrate films.

Podoloff et al., U.S. Pat. No. 5,033,291, Jul. 23, 1991, Flexible Tactile Sensor For Measuring Foot Pressure Distributions And For Gaskets, which discloses a force and pressure sensor having two sets of parallel electrodes which are positioned facing one another and arranged so that electrodes of one set cross the electrodes of the second set at an angle to create a plurality of electrode intersections. Pressure-sensitive resistive material lies between the electrodes at each intersection. An adhesive layer is applied to at least one of the electrode sets in areas between electrode intersections to secure the first and second electrode sets in facing relationship, the adhesive layer preferably being applied in a pattern which provides passages where the adhesive layer does not exist to allow air to escape from interior areas of the electrode set. The thickness of the adhesive layer may be adjusted to permit preloading or to provide a threshold level for the sensor. In order to permit electrodes of the electrode set to be trimmed around their periphery, electrical contact to each electrode of the electrode sets is made intermediate the ends of the electrodes. This is accomplished by providing an insulating layer over the rear of each electrode set having holes therein at the desired intersection points and having a plurality of connecting conductors on the back of the insulating sheet, one for each electrode, which make contact with the corresponding electrode through the hole in the insulating sheet.

Fullen et al., U.S. Pat. No. 5,323,650, Jun. 28, 1994, System For Continuously Measuring Forces Applied To The Foot, which discloses a self-contained system for measuring forces applied to the foot of a user that includes a force sensor array positioned within the user's shoe between the foot and the inner sole of the shoe, the force sensor array including a multiplicity of individual force sensors arranged in a hexagonal pattern that covers the entire area of contact between the sole of the user's foot and the inner sole of the shoe, an electronic circuit module removably attached to the side of the shoe, and a flat interconnecting cable for electrically coupling the force sensor array to the electronic circuit module. The electronic circuit module includes a central processing unit, read-only memory, random access memory, and scanning circuitry for electronically continuously scanning the force sensor array to obtain information indicative of an instantaneous force sensed by each one of the multiplicity of individual force sensors of the force sensor array, for processing that information to obtain force data, and for storing the force data in the random access memory. An annunciator audibly signals the user when a force on the foot greater than a predetermined threshold force is sensed.

In addition to the aforementioned references, the following United States patents disclose devices generally adapted to the measurement of pressures exerted on body parts:

Bourland et al., U.S. Pat. No. 5,010,772, Apr. 30, 1991, Pressure Mapping System With Capacitive Measuring Pad, which discloses a capacitive measuring pad for measuring the pressures exerted by various portions of a patient's body on a mattress. The pad is constructed of transverse conductive strips separated by a compressible insulator to form a matrix of pressure sensitive capacitive nodes. The nodes are repetitively scanned in sequence by a microcomputer to measure their respective capacitances, from which measurements a pressure map is then derived. The resulting pressure map may be displayed on a color graphics monitor with different colors representing different pressures. Node capacitance is found by measuring the response of the node to a driving signal of a known voltage. This measurement is accomplished by connecting one of the node's transverse conductive strips to a sense amplifier. In order to isolate the node of interest from the influence of surrounding nodes, all of the conductive strips except the two intersecting the selected node are connected to ground. Furthermore, the input impedance to ground of the sense amplifier is made negligibly small with respect to the other system impedance. In this way, only the conductive strip connected to the driving source has a voltage impressed on it, and the conductive strips of all other nodes in the system are maintained at ground potential, thus allowing an accurate measurement of the one capacitance.

Tamori, U.S. Pat. No. 5,079,949, Jan. 14, 1992, Surface Pressure Distribution Detecting Element, which discloses a detecting element for sensing surface pressure distributions comprising a substantially rigid insulating substrate, a plurality of scanning row electrodes, formed by metal deposition on said substrate, etched to form a pattern of substantially parallel electrodes which are spaced apart and oriented along a first axis, a thin resistive film, deposited on said substrate, having a resistance which varies as a function of contact area, a substantially resilient deformable surface layer, a plurality of scanning column electrodes, formed by metal deposition on said surface layer, etched to form a pattern of substantially parallel column electrodes which are spaced apart, said surface layer being bonded to said substrate by an anisotropic adhesive so that said column electrodes are oriented along a second axis which is perpendicular to said first axis, said surface layer transmitting pressure distribution to said row electrodes, resistive film, and column electrodes to form a matrix of variable contact resistances to provide analog information relating to the distribution of surface pressure applied to said surface layer.

Rincoe et al., U.S. Pat. No. 5,253,656, Oct. 19, 1993, Apparatus And Method For Monitoring Contact Pressure Between Body Parts And Contact Surfaces, which discloses an apparatus and method for monitoring pressure between the surface of a body part and a contact surface employing a plurality of pressure sensors disposed in a matrix array between the contact surface and the body part. The sensors produce analog force signals proportional to pressure, and a monitor receives the analog signals and produces output signals, preferably digital, having pressure data corresponding to the pressure at each sensor. A computer processor receives the output signals from the monitor to create a force profile for the sensor array. The sensors may be scanned as a read event in variety of manners, including periodic continuous and triggered scanning. Where triggered scanning is desired, one or more switches act to initiate a read event. This monitoring apparatus and method is used, for example, to fit prosthetics, to monitor bed-ridden and wheelchair-bound patients, to reduce paid and sores caused by uneven distribution of pressure and to monitor pressure between a cast and a person. The sensors may be mounted on a single sheet or on strips for positioning along the body, and monitoring is accomplished by multiplexing and digitizing the analog force signals.

In addition to the references cited above, the present inventor disclosed in U.S. patent application Ser. No. 08/254,918, filed Jun. 6, 1994, novel Multi-Directional Piezoresistive Shear And Normal Force Sensors For Hospital Mattresses And Seat Cushions. Although the sensors disclosed in the aforementioned application are an important advancement in the field, the required characteristics of foot pressure sensors are somewhat different from those for hospital mattresses and seat cushions.

In addition to the problem of accurately mapping pressures exerted on human feet, a need exists for performing such measurements on the hooves of animals, particularly horses. Since the substantial weight of a horse is concentrated on relatively small portions of the horse's hooves, it should be the goal of the farrier who fits horseshoes to hooves to trim the hoof in a manner causing the weight of the horse to be distributed relatively uniformly over both those portions of the hoof in contact with the shoes, and those portions in contact with the ground. The present inventor is unaware of any prior art devices that are intended for, or particularly well adapted to, mapping pressures exerted on the hooves of an animal.

OBJECTS OF THE INVENTION

An object of the present invention is to provide an apparatus for measuring pressures exerted on various portions of the bottom of a foot by a shoe, in response to the weight of a body.

Another object of the invention is to provide a two-dimensional pressure sensing array for providing a quantitative two-dimensional map of pressures exerted on various portions of a foot by a shoe or other footwear.

Another object of the invention is to provide a planar piezoresistive pressure sensing array for measuring pressures exerted on various portions of a foot pressing down on the array.

Another object of the invention is to provide a thin, flexible piezoresistive foot pressure sensing array that may be fitted between the upper inner surface of a shoe or other item of footwear, and the lower surface of a foot.

Another object of the invention is to provide a sock containing in the sole surface thereof a thin, flexible array of pressure sensors, the sock being wearable over a foot and providing measurements of pressure exerted on various portions of the bottom of a foot, when the foot is placed in contact with ground or other supporting surface.

Another object of the invention is to provide a sock adapted to fit over the hoof of a horse, the sock having in the sole portion thereof a thin, flexible array of pressure sensors, thus adapting the sock to measuring the pressures exerted on various portions of the bottom of a standing horse's hoof, and thereby providing data permitting a farrier to trim the hoof in a manner resulting in more even distribution of pressures on the horse's hooves.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, I do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends apparatus and methods for measuring the pressures exerted on the bottoms of feet of standing or running humans and animals, particularly horses.

In a basic embodiment of a pressure measuring apparatus according to the present invention, piezoresistive pressure sensors are arranged in a two-dimensional array having an outline shape similar to that of a footprint, and encapsulated in a thin, flexible polymer sandwich. Each sensor includes a resiliently deformable piezoresistive pad, the electrical resistance of which varies inversely with pressure or normal forces exerted on the pad. The piezoresistive sensors are arranged in rows and columns, each of which is electrically conductively connected to a separate wire at the input end of a flexible electrical cable. At the output end of the cable, each wire is connected through a multiplexer to an electrical resistance measuring module such as a bridge. In response to electrical control signals, the multiplexer momentarily connects each piezoresistive sensor in the sensor array to the resistance measuring module, thus producing a sequence of resistance measurements proportional to pressures exerted on various portions of the foot by the array, and thereby permitting the plotting of a two-dimensional map of pressures exerted on the foot.

In the preferred embodiment of pressure sensing arrays according to the present invention, piezoresistive pads are regions of a piezoresistive mesh layer made by impregnating a fabric mesh, preferably made of mono-filament strands of a polymer such as polyester or polyethylene, with a piezoresistive material comprising electrically conductive particles, such as carbon black, suspended in an insulating elastomeric vehicle, such as silicone rubber. The piezoresistive mesh layer is sandwiched between a pair of thin polymeric conductor strip laminations, preferably made of nylon. Inner facing surfaces of the two conductor strip laminations have formed thereon adjacent rows of spaced apart row and column conductors, respectively. Peripheral contacting surfaces of the conductor strip laminations are heat sealed or otherwise bonded to encapsulate the piezoresistive mesh layer, thereby forming a thin, flat, flexible laminated sensor array. Each region of piezoresistive material sandwiched between a row conductor and a column conductor comprises an individual normal force or pressure sensor in a rectangular array of sensors.

In a variation of the basic embodiment of a sensor array according to the present invention, each normal force sensor element constructed as described above is bordered by laterally and longitudinally disposed pairs of shear force sensor elements. The novel shear force sensor according to the present invention comprises a pair of adjacent resilient piezoresistive pads that have longitudinally contacting lateral surfaces. The pads are slidably movable, and when the pads are urged into more or less intimate contact in response to shear forces directed normal to their tangent contact plane, the electrical resistance between the pads varies in a predetermined way as a function of the shear forces. The shear force sensors in the pair laterally adjacent to a normal force sensor preferably have their sensitive axes laterally disposed, while the shear force sensor elements in the longitudinally disposed pair adjacent to a normal force sensor have their sensitive axes longitudinally disposed. This arrangement permits measurement of shear forces in two perpendicular directions in the plane of the sensor array.

In the preferred embodiment of the shear force sensor elements alternating with normal force sensors according to the present invention, each element is fabricated by forming mesh impregnated regions of piezoresistive material that are laterally or longitudinally separated, and in tangential contact along longitudinally or laterally disposed contact zones, respectively.

In another embodiment of the invention, a sock is made of concentric flexible fabric tubes comprising row conductive strips, column conductive strips and piezoresistive normal force and/or shear force sensor elements fabricated similarly to the corresponding parts of the novel planar sensor arrays according to the present invention. Thus constructed, the sock may be fitted over the foot of a person, or hoof of a horse, and measurements made of forces exerted on the foot or hoof, using the force sensing elements contained in the sock.

BRIEF DESCRIPTION OF THE DRAWINGS

FIG. 7A is an upper plan-view of a normal force sensor array of the type shown in FIG. 6, the array being adapted for measuring normal forces exerted on a human foot.

FIG. 7B is a lower plan-view of the sensor array of FIG. 7A.

FIG. 7F is a fragmentary, magnified view of a conductive mesh fabric used in an alternate construction of the array shown in FIG. 7A.

FIG. 7G is a lower plan-view of a lower, row lamination employing the fabric shown in FIG. 7E.

FIG. 7H is a plan-view of a piezoresistive lamination comprising part of the sensor array of FIG. 7A.

FIG. 11 is a rear elevation view of the sensor array of FIG. 7A, in which upper and lower lead-out laminations thereof are folded away from one another.

FIG. 11A is a transverse sectional view of a lower lead-out lamination of FIG. 11, taken along line 11A—11A.

FIG. 12 is an exploded plan-view of an alternate embodiment of a normal force sensor array similar to the one shown in FIG. 7A, in which FIGS. 12A–12E illustrate the lowermost, intermediate, and uppermost laminations comprising the sensor array.

FIG. 13 is an exploded plan-view of a variation of the normal force sensor array shown in FIG. 12, in which FIGS. 13A–13E illustrate the lowermost, intermediate, and uppermost laminations comprising the sensor array.

FIG. 20D is an upper plan-view of the array of FIG. 19.

FIG. 20E is a lower plan-view of the array of FIG. 19.

FIG. 31 is a partly dissected view of the inner, column conductor tube of FIG. 28, showing the tube cut longitudinally and folded flat.

DETAILED DESCRIPTION OF THE PREFERRED EMBODIMENTS

Figure 1:
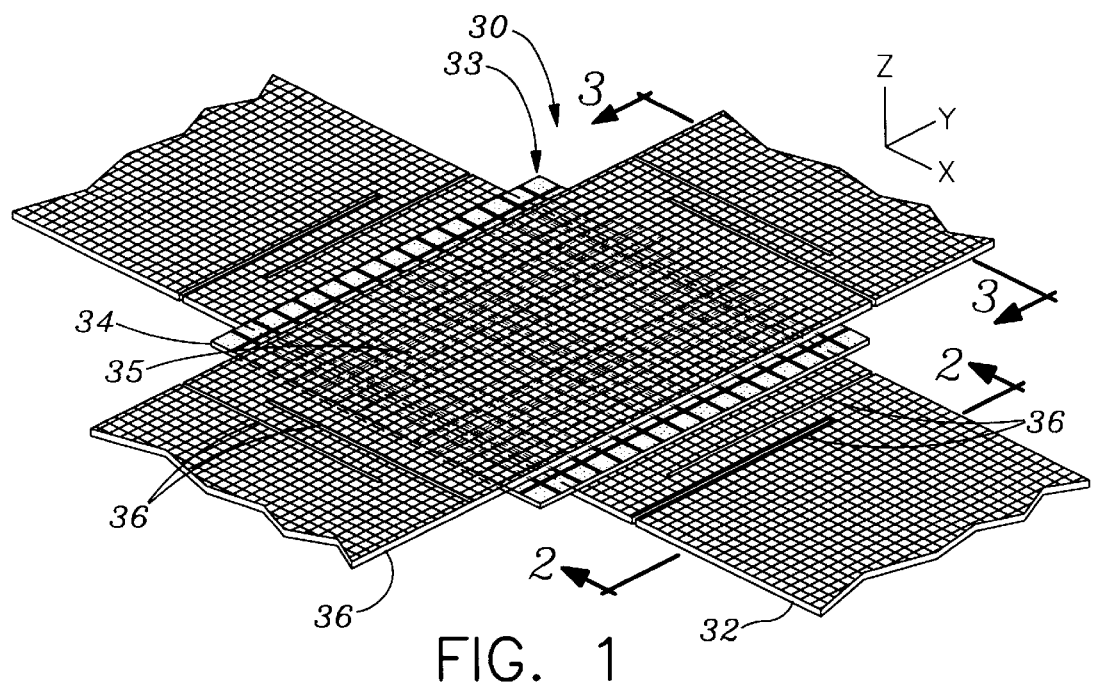
FIG. 1 is an upper perspective view of a normal force sensor element according to the present invention.

Referring now to FIGS. 1–33, piezoresistive foot/hoof pressure measurement apparatus and methods according to the present invention are shown.

Referring first to FIGS. 1–4, a basic embodiment of a piezoresistive normal force sensor element usable to measure foot pressure is shown. As shown in FIGS. 1–4, normal force sensor element 30 includes a first, elongated rectangularly-shaped electrically conductive strip 31 made of a thin, flexible, electrically conductive fabric, such as Flectron brand nickel/copper plated woven nylon mesh fabric made by Monsanto, The Chemical Group, 800 N. Lindberg, St. Louis, Mo. Normal force sensor element 30 also includes a second conductive strip 32 disposed in a plane parallel to first conductive sheet 31. Conductive strip 32 is spaced apart from strip 31 in a direction normal or perpendicular to strip 31. As shown in FIGS. 1–4, conductive sheet 32 is located above strip 31, with its longitudinal axis oriented in a first, X direction, while lower conductive sheet 31 is oriented perpendicularly to the longitudinal axis of the upper sheet in a Y direction. Other orientations of the upper and lower conductive strips are of course possible. Whatever the orientation of conductive strips 31 and 32, sensor element 30 includes a piezoresistive layer 33 sandwiched between the conductive strips. The construction details of piezoresistive layer 33 will now be described.

Figure 4:
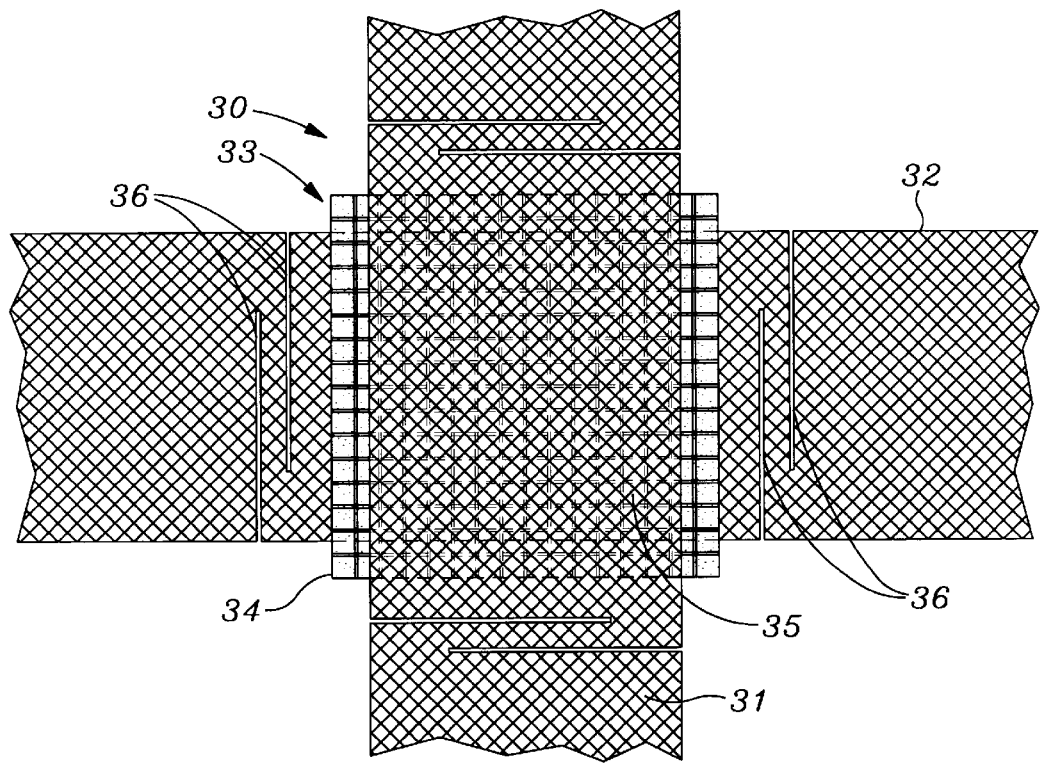
FIG. 4 is a lower plan-view of the sensor element of FIG. 1.

Referring now to FIG. 4, piezoresistive layer 33 of sensor 30 may be seen to preferably include a supporting matrix made of thin, open mesh fabric sheet 34. Fabric sheet 34, which is preferably electrically non-conductive, is preferably woven from monofilament strands of a polymer such as polyethylene or polyester. In an exemplary embodiment of the invention, the present inventor has found that a 300 mesh fabric sheet made of 0.002 inch diameter monofilament strands of polyester proved to be a satisfactory material for fabric sheet 34.

Piezoresistive layer 33 of normal force sensor element 30 is fabricated by impregnating mesh fabric sheet 34 with a resiliently deformable, partially conductive substance 35 that has an electrical resistance inversely proportional to normal forces or pressures exerted on the layer, a property which may be referred to as volume or bulk piezoresistivity. As will become apparent from the ensuing description, partially conductive substance is defined herein as finely divided particles of an electrically conductive material. According to the present invention, mesh sheet 34 is impregnated with piezoresistive substance 35, the mesh providing a durable and dimensionally stable support matrix for piezoresistive substance 35. The present inventor has found that a suitable substance 35 for impregnating mesh 34, thus forming piezoresistive layer 33, is an ink composed of about 50% milled carbon black having a grain size of 2–5 microns, 30% unpolymerized liquid nitrile rubber, type BUNA N, and 20% ABS plastic resin/hardener, or silicone rubber (e.g., Dow Corning RTV 732) and no hardener. Piezoresistive layer 33 is formed by mixing the aforementioned components thoroughly, applying the mixture to a thickness of about 0.004 in. with a spatula, and allowing the mixture to air cure at room temperature.

Figure 5A:
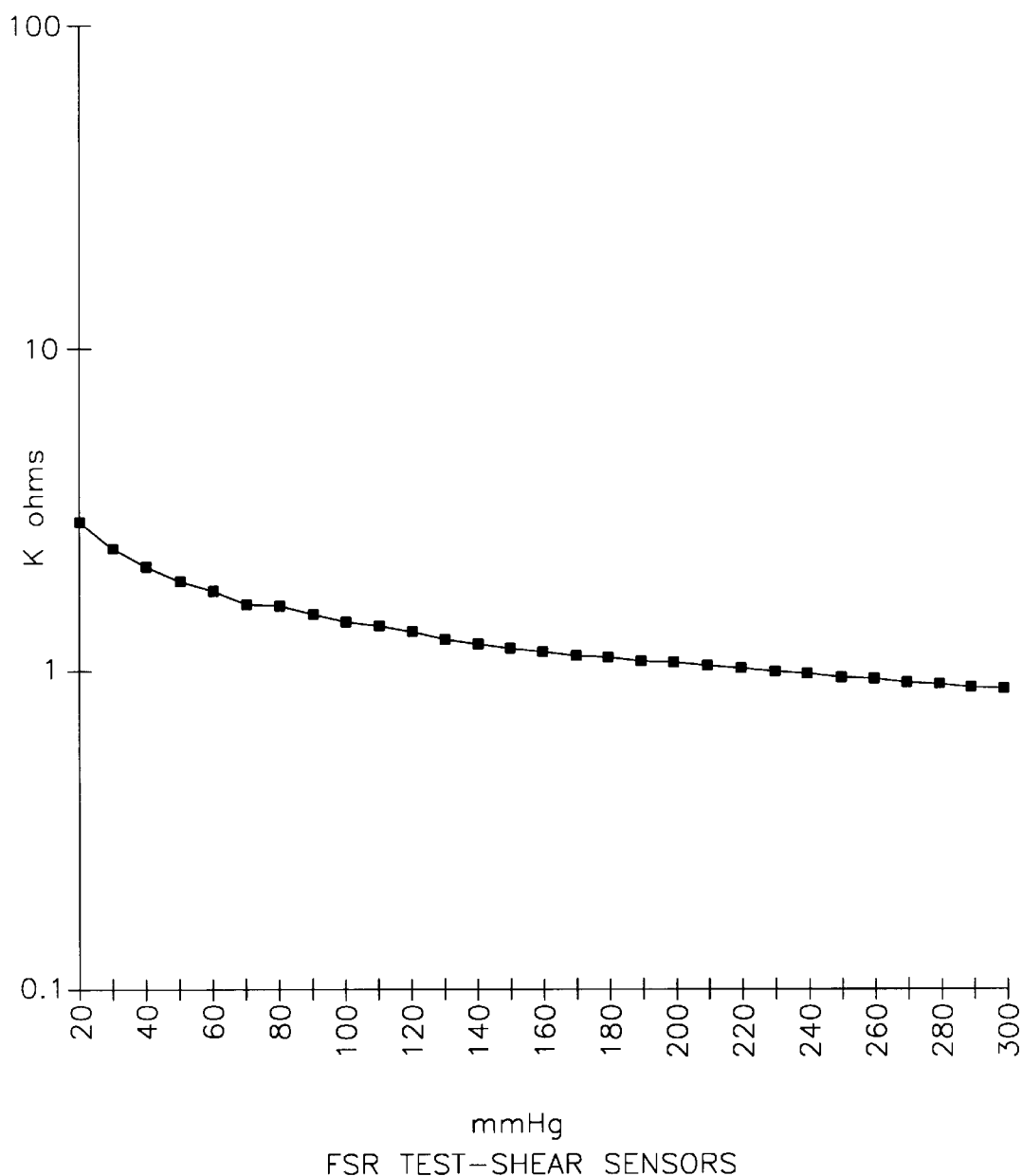
FIG. 5A is a graph of resistance versus normal force or pressure for the sensor element of FIG. 1.

The volume resistivity of piezoresistive layer 33 of normal force sensor element 30 can be varied to a desired cured value by varying the amount of carbon black added to the liquid rubber, and monitoring the resistivity as those two components are being mixed together. The present inventor has found that a suitable range of volume resistivities for piezoresistive layer 33 is about 5 ohm-cm to 100,000 ohm-cm for measurement of normal forces in the approximate range of 0–5 psi, and 100–300,000 ohm-cm for measurement of forces in the approximate range of 5–30 psi. FIG. 5A shows the variation of resistivity versus pressure for a typical sensor element 30.

Figure 6:
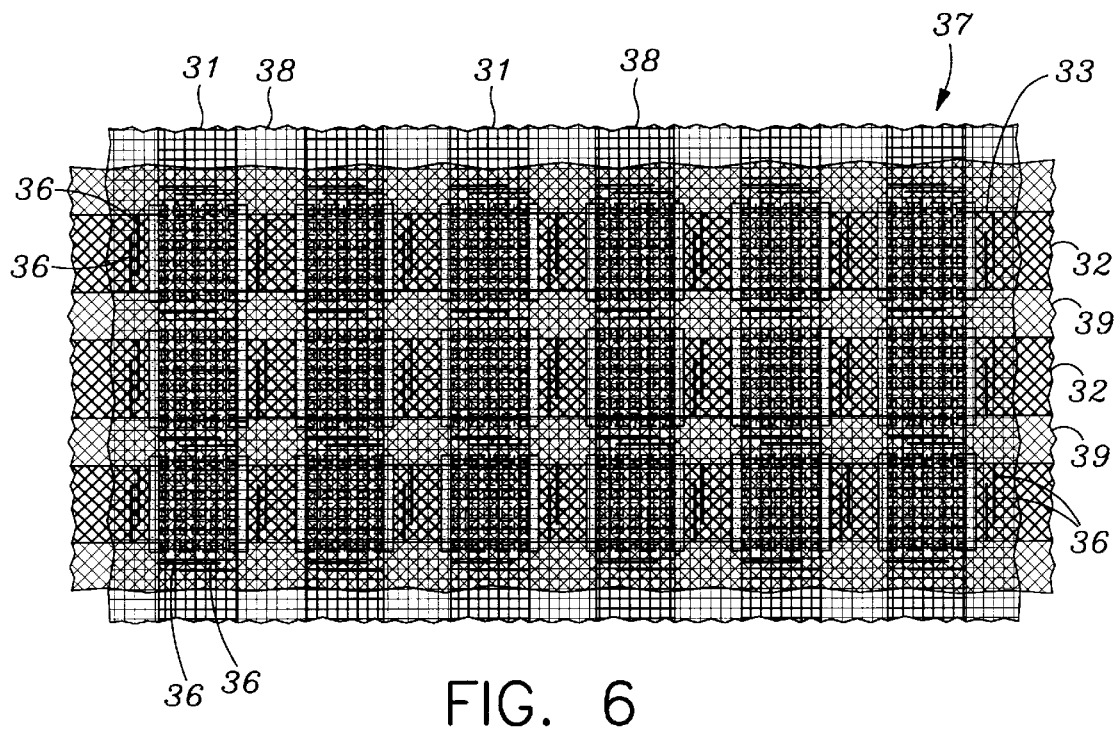
FIG. 6 is a fragmentary upper perspective view of a rectangular array of normal force sensors of the type shown in FIG. 1.

In example embodiments of normal force sensor element 30, conductive strips 31 and 32 were cut from a conductive fabric consisting of nickel/copper coated nylon taffeta and marketed under the brand name FLECTRON by Monsanto, The Chemical Group, 800 N. Lindberg, St. Louis, Mo. This material has a thickness of 3.8 to 4 mils, is flexible and drapable, and has a surface resistivity of less than 0.05 ohms per square. Preferably, each conductive strip 31 and 32 has slits 36 cut perpendicularly inward from opposite longitudinal edges of the strip, to allow stretching of the strip in a direction parallel to its longitudinal axis. As shown in FIG. 1, slits 36 are located in laterally spaced apart pairs, one pair being spaced laterally outwards from each side of piezoresistive layer 33. FIG. 5A illustrates a typical variation of the electrical resistance between lower and electrode conductor strips 31 and 32 of sensor element 30, as a function of pressure or force directed normally to the sensor element, i.e., in the Z direction in FIG. 1. FIG. 6 illustrates a planar array 37 of normal force sensor elements 30 in which a plurality of column conductive strips 31 and row conductive strips 32 form a rectangular matrix of normal force sensor elements. In regions exterior to piezoresistive layers 33 of sensor elements 30, column and row conductive strips 31 and 32 are electrically isolated from one another, to prevent short circuiting, by means of thin column and row insulating strips 38 and 39, respectively. The insulating strips may be made of any suitable electrically insulating material, such as nylon. In the preferred embodiment, insulating strips 38 and 39 are integral with conductor strips 31 and 32, and formed therefrom by photoetching conductive plating on the strips where insulating areas are required.

FIGS. 7A–11 illustrate a normal force sensor array 40 that is particularly well adapted for measuring normal forces or pressures exerted on the bottom surfaces of human feet. Foot pressure sensor array 40 employs normal force sensor elements 50 substantially similar in construction to the normal force sensor elements 30 shown in FIGS. 1–4 and described above, with the sensor elements arrayed in a rectangular array similar to array 37 shown in FIG. 6. However, foot pressure sensor array 40 contains additional novel and advantageous structural and functional features, as will now be described.

Figures 7C, 7D:
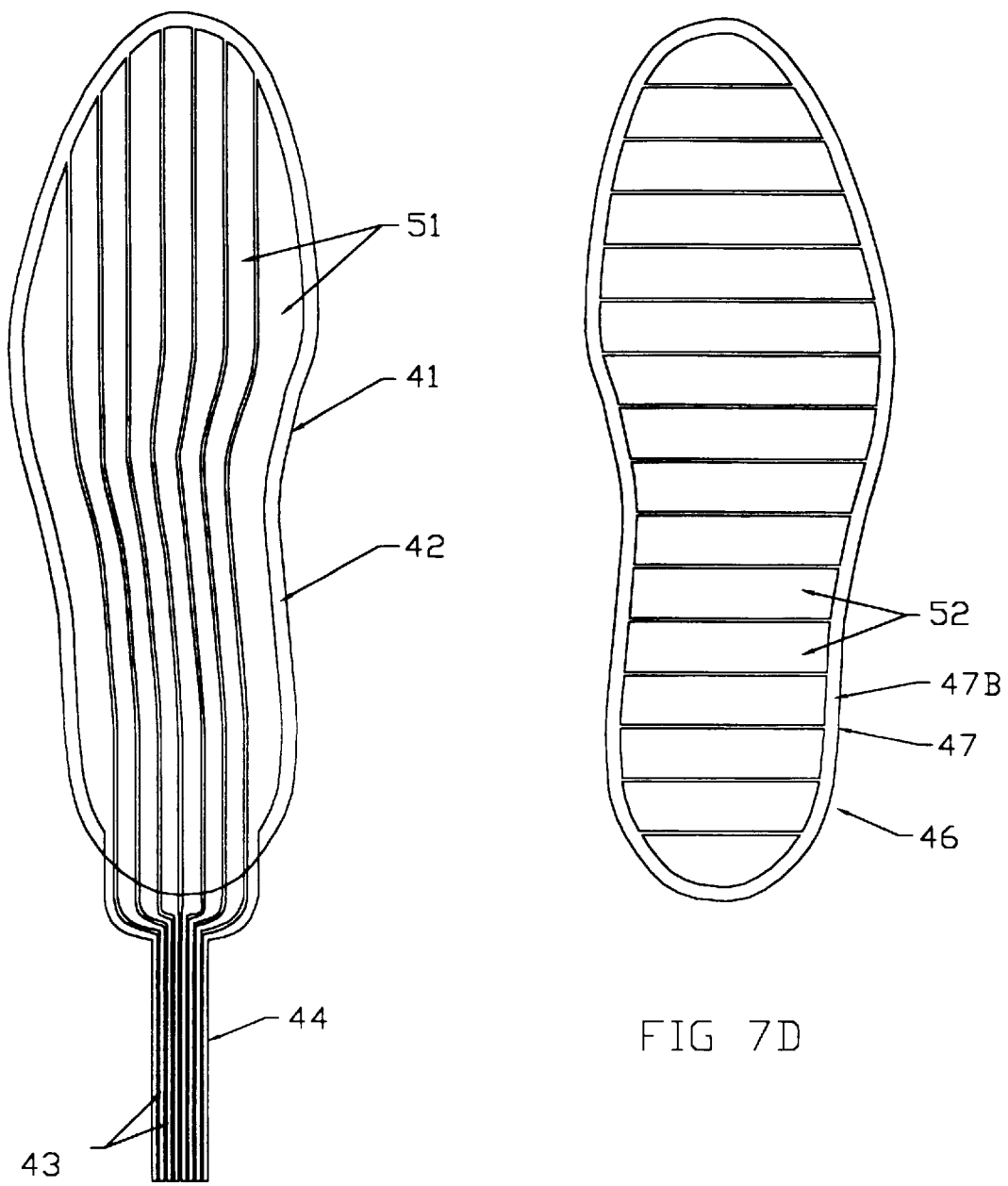
FIG. 7C is a lower plan-view of the upper, column lamination of the array of FIG. 7A.
FIG. 7D is an upper plan-view of the lower, row lamination of the array of FIG. 7A.

Referring now first to FIGS. 7A and 7C, foot pressure sensor array 40 may be seen to include an upper, column conductor strip lamination 41 having a substrate 42 made of a thin, flexible sheet of electrically insulating material such as woven nylon having a thickness of about 4 mils. As may be seen best by referring to FIG. 7A, lamination 41 has the approximate outline shape of a human foot. As may be seen best by referring to FIG. 7C, column lamination 41 has formed on the lower surface thereof a plurality of generally longitudinally disposed, laterally spaced apart column conductive strips 51.

Referring still to FIG. 7C, column conductive strips 51 may be seen to have a generally rectangular, longitudinally elongated plan-view, and are disposed longitudinally between the toe and heel ends of column substrate 42. Preferably, as shown in FIGS. 7A and 7C, the longitudinal edges of conductive strips 51 curve somewhat to parallel the curved longitudinal edges of foot-shaped column substrate 42. As is also shown in FIG. 7C, the width of conductive strips 51 decreases towards the rear of substrate 42, the rear or heel portions of conductive strips 51 tapering or "necking" down into thin rectangular "tail" traces 43. Preferably, this necking down is located close to the rear edge of the heel portion of substrate sheet 42, to ensure that sensor elements 50 will have sufficient area to be operable as close as possible to the heel edge of sensor array 40.

Figure 10:
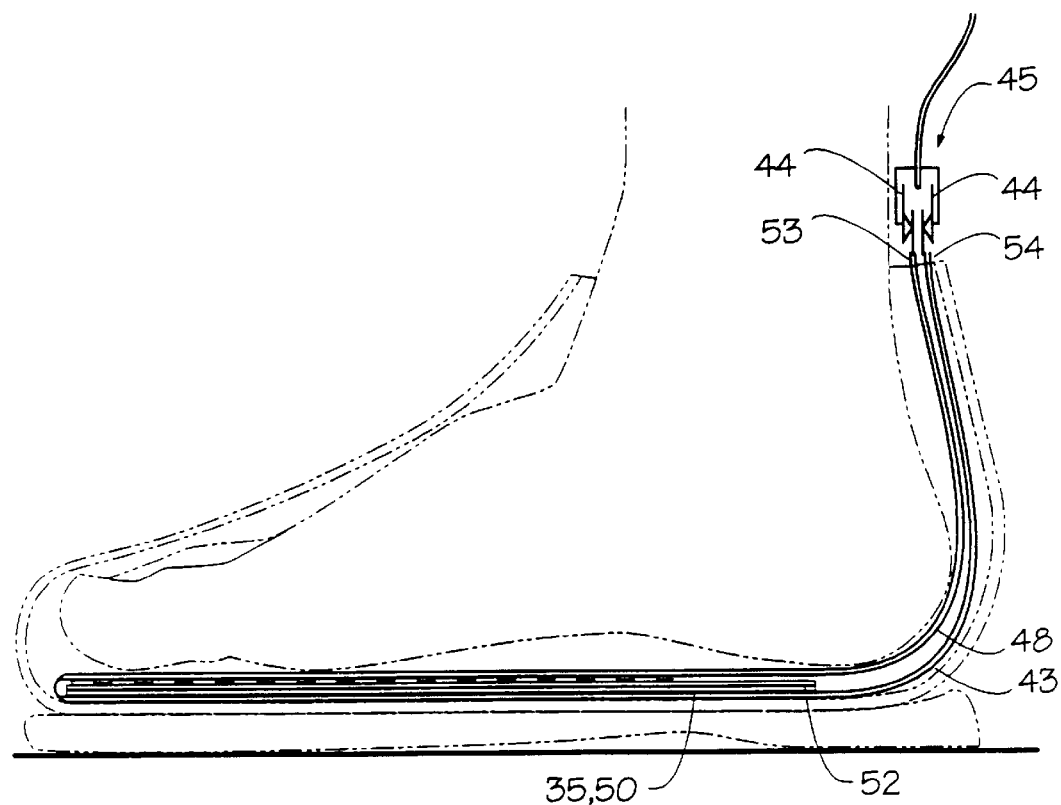
FIG. 10 is an expanded side sectional view of the sensor array of FIG. 7A, showing the array bent to fit in a shoe.
Figure 30:
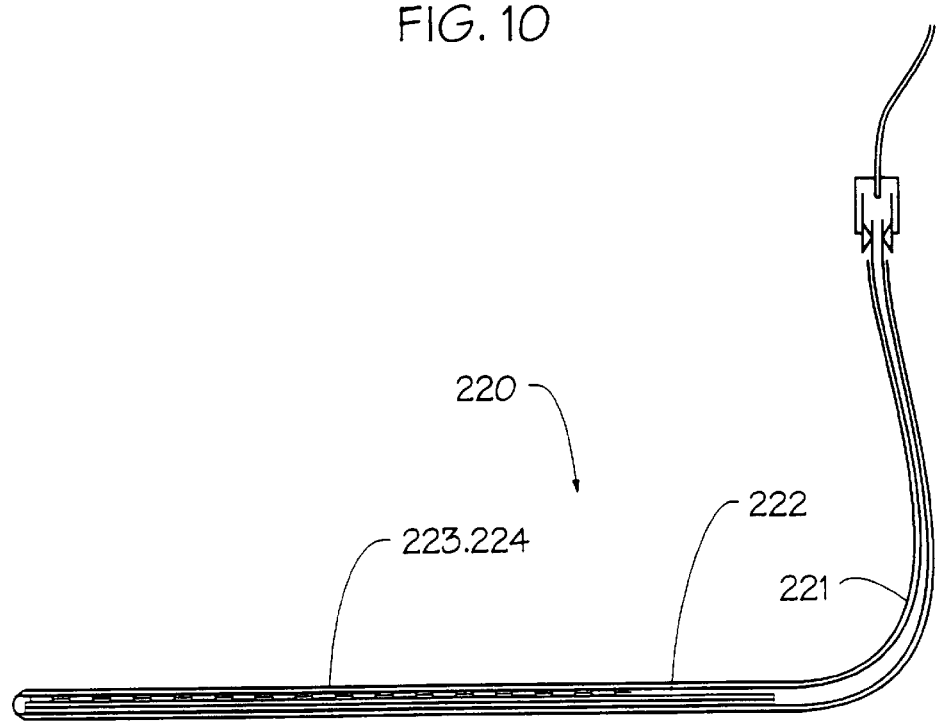
FIG. 30 is a view similar to that of FIG. 29, but showing the sock in a folded position.

As shown in FIGS. 7A and 7B, column substrate 42 preferably has an integral, rectangularly-shaped tab or tongue 44 that protrudes rearward from the heel edge of the substrate sheet. Tongue 44 provides support for traces 43, and has a transversely disposed rear edge adapted to be insertably received by a ribbon cable connector 45, as shown in FIG. 10.

As may be seen best by referring to FIG. 7D, sensor array 40 may be seen to include a lower, row conductor strip lamination 46 having a substrate 47 made of a sheet of a thin, flexible electrically insulating material such as woven nylon having a thickness of about 4 mils. Row conductor strip lamination 46 preferably has the same foot-shaped outline as column conductor strip lamina 41. As shown in FIG. 7D, row conductor strip lamination has formed on the upper surface thereof a plurality of generally laterally disposed, longitudinally spaced apart row conductive strips 52.

Referring still to FIG. 7D, row conductive strips 52 may be seen to have a generally rectangular, laterally elongated plan-view shape, and are disposed laterally between inner and outer longitudinal edges of shoe-shaped row substrate 47.

An individual electrical connection is made to each row of conductor strips 52 by a separate longitudinally disposed conductive trace 48, as follows.

Figure 7E:
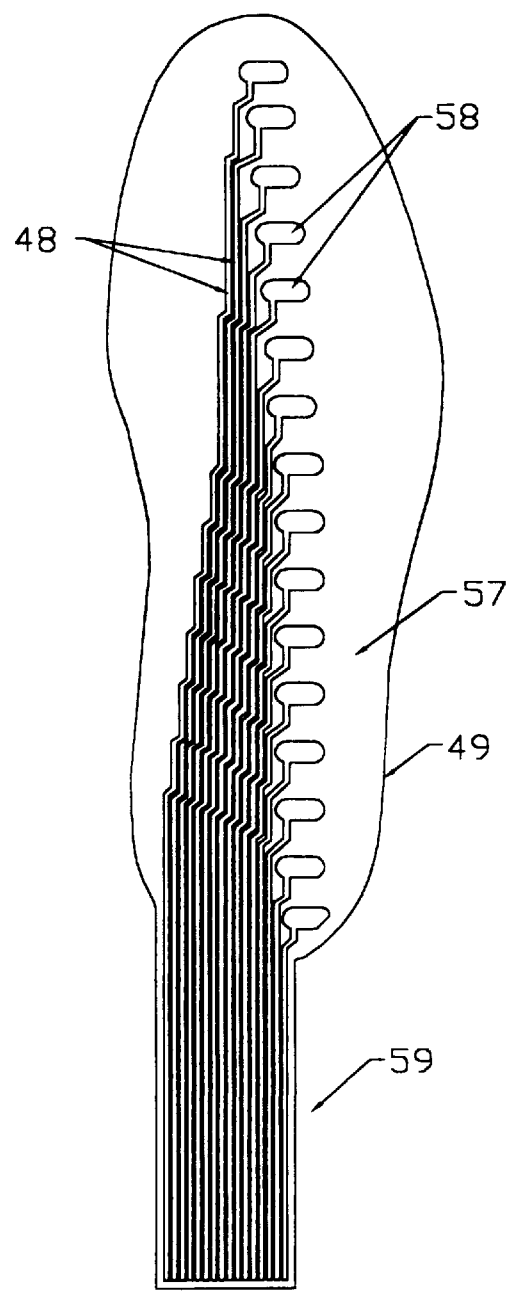
FIG. 7E is an upper plan view of a row lead-out lamination used to make electrical connections to the row lamination of FIG. 7D.
Figure 7I:
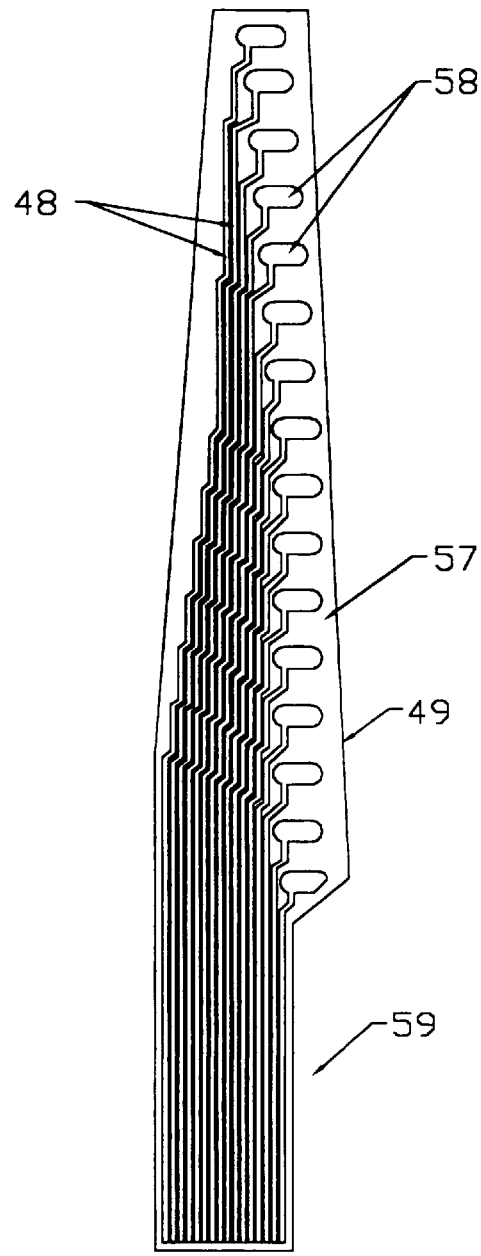
FIG. 7I is a fragmentary upper plan view of the lead-out lamination of FIG. 7E.
Figure 8:
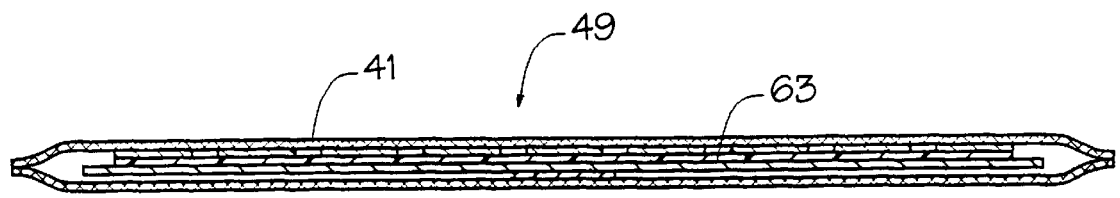
FIG. 8 is a transverse sectional view of the sensor array of FIG. 7A, taken along line 8—8.
Figure 9:
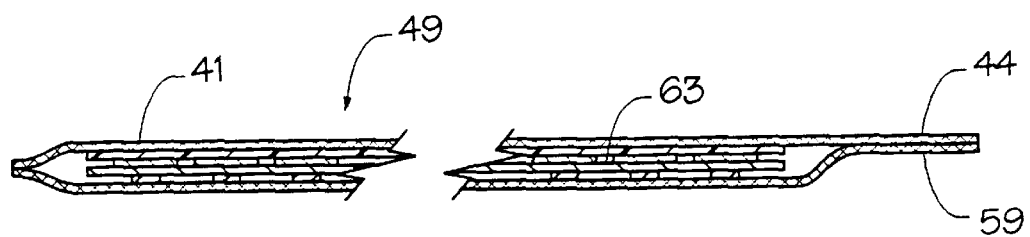
FIG. 9 is a longitudinal sectional view of the sensor array of FIG. 7A, taken along line 9—9.

Referring now to FIG. 7E, it may be seen that row conductor strip lamination 46 is overlain by a thin, longitudinally elongated, lead-out lamination 49, having a thin, flexible insulating substrate 57. As shown in FIG. 7A, lead-out substrate 57 is longitudinally disposed over the central longitudinal portion of row conductor strip lamination 46. Substrate 57 is fastened to the upper surface of row conductor lamination 46 by any suitable means, such as adhesive regions 58 between the lower surface of the lead-out substrate and the upper surface of the row conductor lamination.

As shown in FIG. 7E, a plurality of thin, narrow longitudinally elongated, rectangular-shaped lead-out traces 48 are adhered to the upper surface of lead-out lamination 49. Lead-out traces 48 are laterally spaced apart from one another, and terminated at the upper or toe end thereof by a laterally elongated, oval plan-view "flag" appendage 58 that is in electrically conductive contact with the lead-out trace. Flags 58 protrude laterally outwards from a longitudinal edge of lead-out lamination 49, and are longitudinally aligned and spaced apart so as to each be centered over a separate row conductor strip 52. Each flag conductor 58 is conductively coupled to a separate row conductor strip 52. In the preferred embodiment, flag conductors 58 are adhered to row conductor strips 52 by an electrically conductive adhesive such as R17012 neoprene-type adhesive, manufactured by Stockwell Rubber Company, 4749 Talbut Street, Philadelphia, Pa. 19139.

Referring still to FIG. 7E, lead-out lamination 49 may be seen to have an integrally formed rectangular tongue 59 that protrudes rearward from the heel edge of the substrate sheet. Tongue 59 provides support for row lead-out traces 48, and has a transversely disposed rear edge adapted to be insertably received by ribbon cable connector 45.

In the embodiment of normal force sensor array 40 employing upper column, conductor lamination 41 and lower, row conductor lamination 46 constructed as described above, the lead-out traces 43 and 48 are on the lower and upper facing surfaces of the respective laminations. Thus, the rearwardly protruding tongues 44 and 59 supporting the lead-out traces must be bent away from one another to prevent the upper and lower traces from contacting one another, and to permit separate electrical connections to be made to the respective row and column lead-out traces.

In this embodiment of the row, column and lead-out laminations of normal force sensor array 40, each of the laminations was fabricated as photo-etched printed circuits from a thin sheet of 0.002 inch thick rip-stop nylon having on one surface thereof a layer of electroless deposited copper. The copper-coated sheet was cut to the desired plan-view shape, as shown in FIGS. 7A and 7B, and the copper layer coated with a photo-sensitive, photo-resist emulsion. Next, a photographic film positive containing an image of a desired conductor pattern, e.g., column conductive strips, row conductive strips, or lead-out conductive strips or traces was placed in contact with the photo-sensitized surface, and exposed to light. The exposed substrate was then placed in a solvent bath to remove the non-exposed emulsion, and subsequently placed in an ammonium persulfate bath to etch away the copper from those regions of the substrate where no conductors paths appear. The exposed copper conductors on the surface of the substrate were then plated with nickel in an electroless bath, to reduce the oxidation rate of the exposed copper surfaces, and to increase the mechanical strength of the conductive strips on the substrate.

In a variation of the photo-etched construction of the column, row and lead-out substrates described above, the copper coated nylon sheet was overcoated with an electroless deposited layer of nickel prior to photo-etching. In this case, a ferrous chloride etching solution was used to remove both copper and nickel from non-conductive portions of the substrates. In both cases, it was found that a suitable material for the substrate was copper coated or copper and nickel coated nylon having a thickness of about 0.004 inch and a total plating thickness of about 0.002 inch.

In the preferred embodiment of normal force sensor array 40, upper and lower laminations 41 and 46 are fabricated by a novel construction that allows lead-out traces to be on outer, upper and lower surfaces of the upper and lower laminations, respectively, rather than on inner, facing surfaces. The novel construction eliminates the requirement for separate electrically conductive feed-throughs required by conventional two-sided printed circuits, as will now be described.

According to the present invention, a novel construction of upper and lower laminations 41 and 46 utilizes a substrate made of a material consisting of woven mesh of non-conductive strands, in which all of the outer surfaces of each of the strands are plated with a conductive material. An example of such a material is Flextron brand nickel/copper plated nylon mesh fabric, part number 3050-226, manufactured by Monsanto.

The aforementioned material has substantial electrical conductivity through its thickness dimension as well as in the plane of the fabric. Therefore, as shown in FIGS. 7F and 11A, the material M may have insulating paths P etched entirely through the thickness dimension of the substrate, thus forming conducting islands, such as A and B, having identical upper and lower conductive regions that are in electrical contact with one another. In this embodiment, as shown in FIG. 7G, row connector lead-out lamination 49 is attached to the lower, outer side of row conductor strip lamination 46, rather than to the upper, inner side of the lamination. This arrangement permits inner facing surfaces of laminations 41 and 46 to have row or column conductive strips electrically in contact with lead-out strips on the outer surfaces of tongues 44 and 49. With an insulating sheet 44A slid between the inner facing surfaces of the tongues to prevent short circuiting, as shown in FIG. 10, the two tongues may be inserted into a single edge card connector 45 provided with upper and lower connectors contacting upper and lower lead-out traces, respectively.

Referring now to FIGS. 8–11 in addition to FIGS. 7A, 7B, and 7H, normal force sensor array 40 may be seen to include a piezoresistive lamination 63 sandwiched between row conductor lamination 46 and column conductor lamination 41. Piezoresistive lamination 63 can be comprised of individual, generally rectangularly-shaped piezoresistive cells similar to piezoresistive layers 33 shown in FIGS. 1–4 and described above. Preferably, however, piezoresistive lamination 63 of sensor array 40 is fabricated as a unitary lamination forming an array of rectangular sensor elements 63A.

Thus, as shown in FIGS. 7H and 8–11, an example piezoresistive lamination 63 of sensor array 40 includes a mesh fabric matrix sheet 64 made of a 300 mesh fabric woven from 0.002 inch diameter mono-filament strands of polyester fiber and cut to the same plan-view outline shape as that of column substrate 42 and row substrate sheet 47, but of slightly smaller size. In an example embodiment tested by the present inventor, matrix sheet 64 had an outer perimeter that was inset about $\frac{1}{16}$th inch from the perimeter of column substrate 42 and row substrate 47, forming a border 65 of the same width. As will be described below, this perimeter border facilitates encapsulating piezoresistive lamination 63.

In an example embodiment of normal force sensor array 40, mesh fabric matrix sheet 64 was cut from a 300 mesh fabric sheet made of 0.002 inch diameter monofilament strands of polyester. Matrix sheet 64 was impregnated with an elastomeric piezoresistive substance 66 having a volume resistivity of about 120,000 ohm-cm, a composition of 50% carbon and 50% RTV 732 silicone rubber and a thickness of about 0.002 inch. The present inventor has found that a suitable method for impregnating matrix sheet 64 with piezoresistive substance 66 is by spreading the substance in the form of a viscous, uncured paste, using a spatula similar to those sometimes used in screen printing.

After piezoresistive lamination 63 has been fabricated as described above, and piezoresistive substance 66 allowed to cure at about 20° C. for about 4 hours, the lamination is positioned concentrically between row substrate 47 and column substrate 42. The peripheral borders 47B and 42B of the row and column substrates are then pressed firmly together and thermally fused to one another by the application of heat and pressure, thus hermetically encapsulating piezoresistive lamination 63. So constructed, sensor array 40 is impervious to the effects of moisture and air.

In an alternate construction that seals piezoresistive lamination 63 between row and column substrates 47 and 42 against moisture and air, the three laminations are positioned between upper and lower latex rubber sheets 53 and 54, as shown in FIG. 10. Upper and lower latex sheets 53 and 54 have a plan-view shape similar to the plan-view shapes of the substrate, but are slightly larger, providing upper and lower border areas, respectively, that may be sealed to each other. In a preferred embodiment of the alternate construction, the latex sheets have a thickness of about 0.004 inch, and are sealed to each other by strips of two-sided (double-stick) adhesive tape, such as 3M 950.

In the embodiments of foot pressure sensor array 40, shown in FIGS. 7A–7H, the sensor array includes an upper column, conductor strip lamination 41 and a lower, row conductor strip lamination 46 having the shape of a left human foot, thus adapting the sensor array to be placed in a shoe to measure pressures exerted on a person's left foot. A mirror image sensor array having upper column conductor could be constructed for measuring pressures on the right foot. However, the present inventor has found that a single type sensor array may be used for both left and right feet by turning over the array as required.

FIGS. 12A–12E illustrates an alternate embodiment of the foot pressure or normal force sensor array 40 shown in FIGS. 7A–11 and described above. The alternate embodiment employs a novel construction using an aperture mask lamination which eliminates the need for conductively adhering lead-out lamination trace termination flags to row conductive strips, as will now be described.

Referring first to FIG. 12A, foot pressure sensor array 300 may be seen to include a bottom, column conductor strip lamination 301 comprising a insulating substrate sheet 302 on which are formed a plurality of longitudinally disposed, laterally spaced apart column conductive strips 311. Column conductive strips 311 terminate at the rear or heel end of substrate 302 in narrowed-down conductive lead-out traces 303 located on a rearwardly protruding, rectangularly-shaped tab or tongue portion 304 of substrate sheet 30. Preferably, column conductive strip lamination 311 is made from an etched-through fabric sheet, as shown in FIG. 7F and described above. Using this arrangement, the conductive lead-out traces 303 are electrically continuous through the thickness dimension of the substrate sheet 302, allowing electrical contact to be made to the lead-out traces by lower contacts of a ribbon cable connector 305.

Referring now to FIG. 12B, sensor array 300 may be seen to include a piezoresistive lamination 323. Piezoresistive lamination 323 comprises a mesh matrix sheet 324 supporting a piezoresistive substance 326, in a construction substantially similar to that of piezoresistive lamination 63 described above. Preferably, matrix sheet 324 of piezoresistive lamination 323 has a rearwardly protruding tongue 324A which provides electrical insulation between column conductive traces 303 below the piezoresistive lamination, and the lamination above it.

Referring now to FIG. 12C, sensor array 300 may be seen to include a row conductor strip lamination 306 having an insulating substrate sheet 307 made of a thin, flexible, electrically insulating material. Row conductor strip lamination 306 has formed on a surface thereof a plurality of generally rectangularly shaped, laterally disposed, longitudinally spaced apart row conductive strips 312. Preferably, row conductive strip lamination 306 is made from an etched-through mesh fabric sheet, as shown in FIG. 7F and described above. With this arrangement, the lower surfaces of row conductive strips 312 may be in electrical contact with piezoresistive layer 323, while lead-out connections may be made to the upper surfaces of the conductive strips protruding upwards through the mesh substrate sheet 307. The novel manner of making the aforementioned connections will now be described.

Referring now to FIG. 12D, sensor array 300 may be seen to include an aperture mask lamination 314, made of a thin sheet of flexible, electrically insulating material such as Mylar or nylon. Aperture mask lamination 314 consists of a sheet 315 of the above-described material, that has been cut to the same plan-view shape as column and row lamination substrates 302 and 307. A plurality of laterally elongated, longitudinally aligned and spaced apart apertures 316 is provided through the thickness dimension of sheet 315. One such aperture 316 is longitudinally centered on the laterally disposed center line of each row conductive strips 312, when aperture mask lamination 314 is stacked on top of row conductor strip lamination 306. Thus located, apertures 316 allow electrically conductive contact to be made through insulating substrate 315 to the row conductors 312, by a lead-out lamination located above the substrate, as will now be described.

Referring now to FIG. 12E, sensor array 300 may be seen to include a lead-out lamination 309, made of a thin substrate sheet 317 of electrically insulating material, cut to approximately the same plan-view shape as aperture mask lamination 309.

A plurality of thin, narrow conductive lead-out traces 308 are provided on a surface of substrate sheet 317. Lead-out traces 308 are laterally spaced apart from one another, and each is terminated at the upper end thereof by a laterally elongated, oval plan-view "flag" appendage 318 that is in electrically conductive contact with the lead-out trace. Flags 318 of lead-out lamination 309 protrude laterally outwards from corresponding lead-out traces 308, and are so located as to each be vertically aligned with a separate aperture 316 of aperture mask lamination 314, with the lead-out lamination overlying and vertically aligned with the aperture mask lamination. Therefore, when lead-out lamination 309 is pressed down and adhered to aperture mask lamination 314, flags 318 conductively contact row conductor strips 312.

Preferably, lead-out lamination 309 is made from an etched-through mesh fabric sheet, as shown in FIG. 7F and described above. With this arrangement, the lower surfaces of flags 318 may be in conductive electrical contact with row conductor strips 312, while lead-out traces 308 on the upper surface of lead-out substrate 317 may be electrically contacted by upper contacts of a ribbon cable connector 305.

Laminations 301, 323, 306, 314, and 315 are stacked vertically and sealed together by 3M double-stick tape to form foot pressure sensor array 300.

FIGS. 13A–13E illustrate a modification of the alternate embodiment 300 of the foot pressure sensor array depicted in FIGS. 12A–12E and described above. Modified foot pressure sensor array 300A shown in FIGS. 13A–13E is substantially identical in structure and function to sensor array 300 shown in FIGS. 12A–12E and described above, except for the spacing between row conductor strips 312A, and corresponding apertures 316A and flags 318A. By varying the longitudinal spacing between row conductor strips 312A, modified foot pressure sensor array 300A may be constructed so as to have thinner, more densely spaced conductor strips where greater sensitivity and spatial resolution are required, such as toe region T and heel region H identified in FIG. 13. Conversely, conductive strips 312 may be wider and less densely spaced in regions such as instep region I where less sensitivity and spatial resolution are required.

Figure 14:
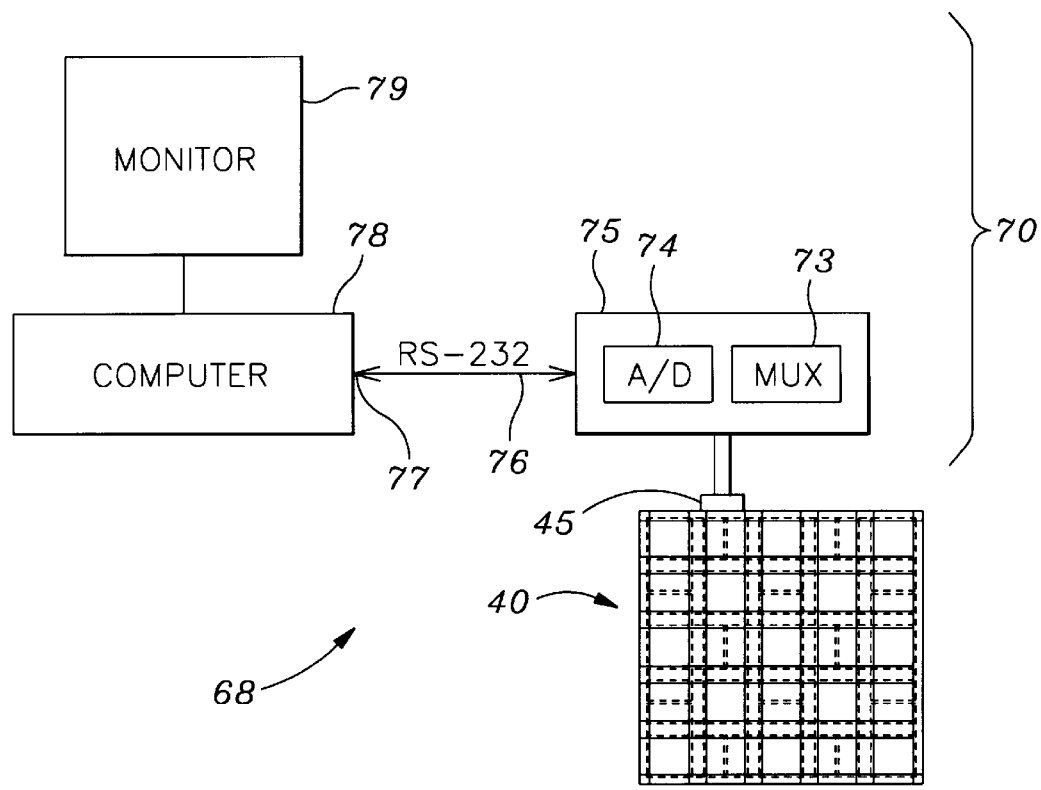
FIG. 14 is a partially diagrammatic block diagram of the sensor array of FIG. 7A, showing the array interconnected with processing and display circuitry.
Figure 2:
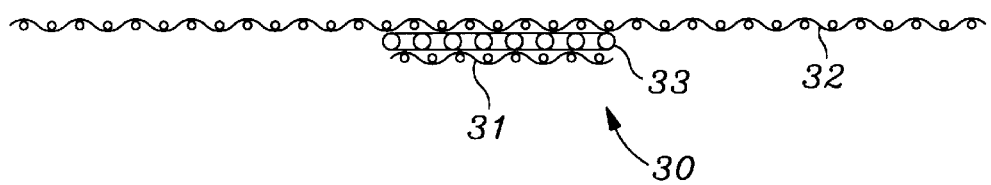
FIG. 2 is a first transverse sectional view of the sensor element of FIG. 1, taken along line 2—2.
Figure 3:
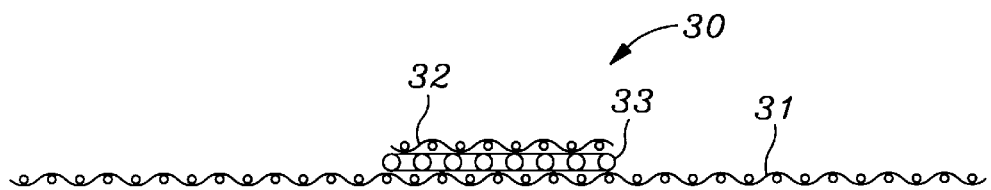
FIG. 3 is a second transverse sectional view of the sensor element of FIG. 1, taken along line 3—3.

FIG. 14 is a partially diagrammatic view of a planar foot pressure measuring and mapping apparatus 68 according to the present invention. As shown in FIG. 14, apparatus 68 includes a foot pressure sensor array 40 comprised of sensor elements 30 of the type shown in FIG. 1, and signal processing and display circuitry 70. In the preferred embodiment, foot pressure sensor 40 is connected to signal processor and display circuitry 70 by means of a thin, flat, flexible multi-conductor ribbon cable 71 that is terminated at one end thereof by ribbon cable connector 45. As was described previously and shown in FIG. 10, ribbon cable connector 45 is adapted to insertably receive rearwardly protruding tongue 44 of sensor 40, and has individual conductors that frictionally and electrically conductively contact a separate one of each of the row and column lead-out conductor traces on the upper and lower surfaces of the tongue.

As shown in FIG. 14, interface cable 71 is connected at the other end thereof to an interface module 72 containing means for applying an electrical sampling signals between a selected column conductive strip 51 and a selected row conductor strip 52, to measure the resistance value of selected sensor element 30. Resistance is measured by applying a known voltage across a sensor resistance element, and measuring the resulting current, or applying a known current, and measuring the voltage drop. Although a d.c. sampling signal may be used for measuring resistances of sensor elements 30, preferably, an a.c. signal is used, to avoid polarizing effects on the sensor elements.

Interface module 72 preferably contains a multiplexer 73, which sequentially outputs a sequence of mxn signals, each signal being representative of the resistance value for a particular sensor element 30 at the intersection of the mth row conductive strip with the nth column conductive strip. Also in the preferred embodiment, an analog-to-digital converter (ADC) 74 is connected between an analog resistance measuring circuit 75 and multiplexer 73, which is then of the digital variety, outputs a serial digital data signal on an RS232 port 76. In the preferred embodiment, RS232 port 76 of interface module 72 is connected to serial data port 77 of a computer 78.

Computer 78 is used to control interface module 72, directing the sequence of addressing sensors 30 in array 40.

Computer 78 also performs signal processing functions, using predetermined scaling factors to convert the resistance values of sensor elements 30 to digital values representing normal forces and pressures exerted on the sensors. In the preferred embodiment, digital numbers representing the pressures on each of the mxn sensors 30 in array 40 are utilized to produce area maps of those pressures, which are displayed on a monitor 79 and stored in digital memory if desired.

FIGS. 15–18 illustrate a shear force sensor element 80 according to the present invention. For reasons to be stated later, it would be desirable in some applications to be able to measure shear forces as well as normal forces or pressures exerted on a foot.

Figure 16:
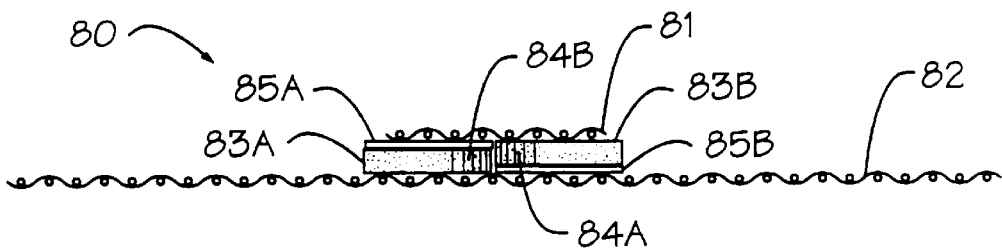
FIG. 16 is a first transverse sectional view of the sensor element of FIG. 15, taken along line 16—16.
Figure 15:
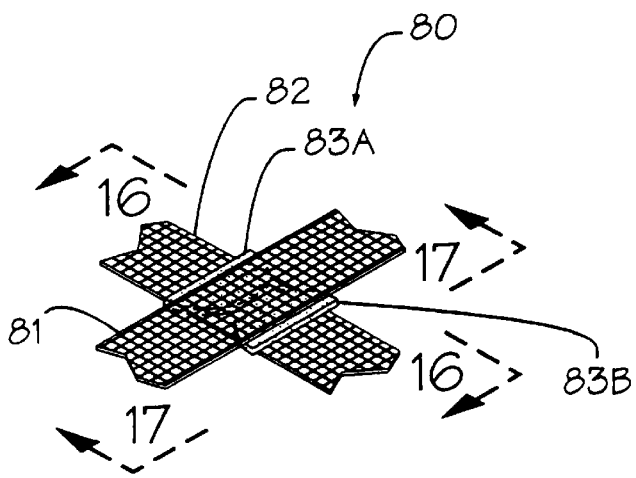
FIG. 15 is an upper perspective view of a shear force sensor element according to the present invention.
Figure 17:
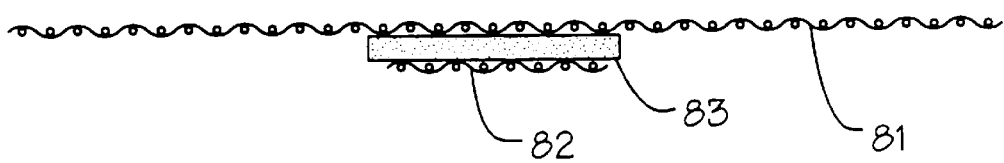
FIG. 17 is a second transverse sectional view of the sensor element of FIG. 15, taken along line 17—17.

Referring now to FIGS. 15–18, but especially to FIGS. 15 and 16, shear force sensor element 80 may be seen to include a first elongated, rectangularly-shaped electrically conductive strip 81 made of a thin flexible, electrically conductive fabric, such as Flectron. Shear force sensor element 80 also includes a second conductive strip 82 spaced apart from strip 81 in a direction normal or perpendicular to strip 81.

Shear force sensor element 80 includes at least one pair of elastomeric piezoresistive pads 83A and 83B located between conductive strips 81 and 82. As may be seen best by referring to FIGS. 13 and 14, piezoresistive pads 83A and 83B have surfaces 84A and 84B, respectively, which tangentially contact one another. Pad 83A is in electrically conductive contact with lower conductive strip 81, and pad 83B is in electrically conductive contact with upper conductive strip 82. Thus, when contacting surfaces 84A and 84B of pads 83A and 83B are urged into more intimate contact in response to shear forces directed normal to their tangent contact plane, the electrical resistance between the conductive strips is reduced, a phenomenon which may be referred to as tangential or surface piezoresistivity.

As shown in FIG. 16, to electrically isolate lower piezoresistive pad 83A, which is conductively coupled to lower conductive strip 81, from upper conductive strip 82, a thin, flexible insulating sheet 85A is positioned between that portion of the lower surface of the upper conductive strip that overlies pad 83A, and the upper surface of the pad. In the preferred embodiment, insulating sheet 85A is made of a slippery material such as TEFLON, the lower surface of the sheet thereby facilitating sliding lateral motion of lower piezoresistive pad 83A relative to upper conductive strip 82, in response to lateral or shear forces exerted on lower strip 81 relative to upper strip 22. Similarly, a slippery insulating sheet 85B is located between the upper surface of lower conductive strip 81 and upper piezoresistive pad 83B, to electrically isolate upper piezoresistive pad 83B from lower conductive strip 81, while permitting slidable motion of the pad with respect to the strip.

Figure 18:
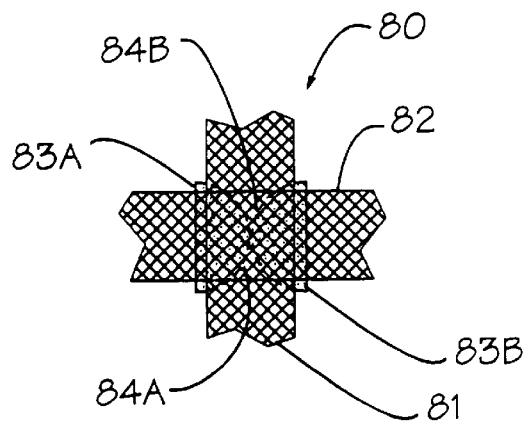
FIG. 18 is a lower plan-view of the sensor element of FIG. 15.
Figure 18A:
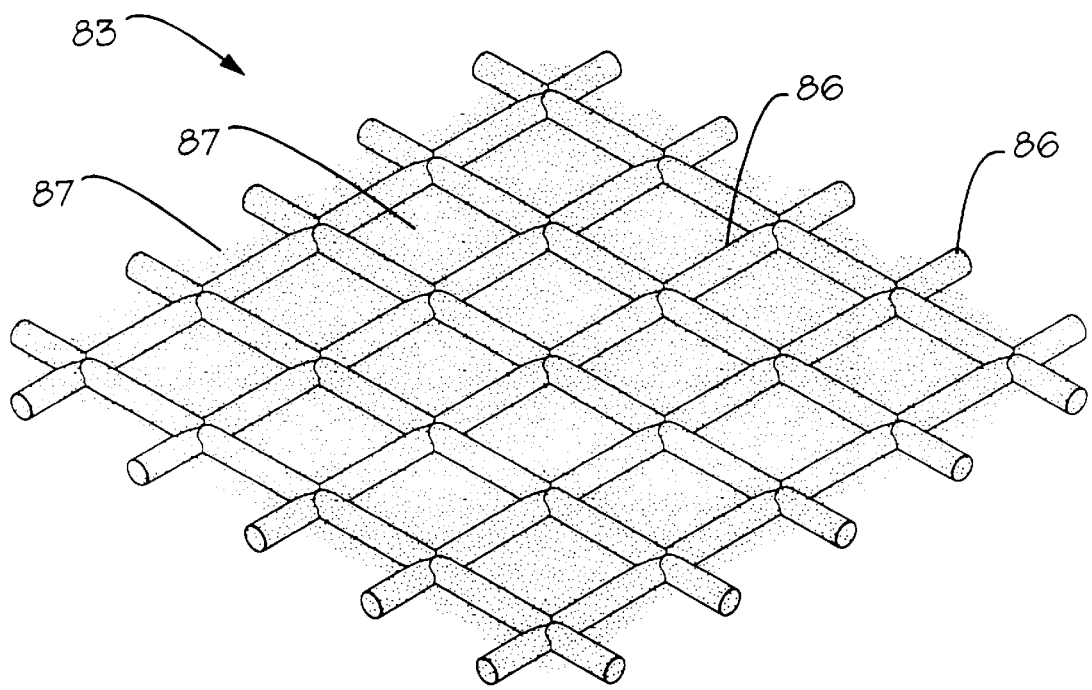
FIG. 18A is a fragmentary, magnified view of a piezoresistive pad comprising part of the shear force sensor element of FIG. 15, the pad being fabricated from a mesh fabric.

Referring now to FIGS. 15, 16 and 18A, each piezoresistive pad 83 of shear force sensor element 80 may be seen to preferably include a supporting matrix made of a thin, open mesh fabric sheet 86. Fabric sheet 86, which is preferably electrically non-conductive, is preferably woven from mono-filament strands of a polymer such as polyethylene or polyester. In an example embodiment of shear force sensor element 80, fabric sheet 86 was a 300 mesh fabric sheet made of 0.002 inch diameter mono-filament strands of polyester.

Mesh fabric sheet 86 is impregnated with a resiliently deformable, partially conductive substance 87 that has an electrical resistance inversely proportional to compressive forces exerted on the surfaces 84 of the pads in response to shear forces on the pads, mesh sheet 86 provides a durable and dimensionally stable support matrix for piezoresistive substance 87. The present inventor has found that a suitable piezoresistive substance 87 for impregnating mesh 86, thus forming piezoresistive pad 83, is an ink composed of about 50% milled carbon black having a grain size of 205 microns, 30% unpolymerized liquid nitrile rubber, type BUNAN, and 20% ABS plastic resin/hardener, or silicone rubber (e.g., Dow Corning RTV 732) and no hardener. Piezoresistive pads 83 are formed by mixing the aforementioned components thoroughly, applying the mixture to a thickness of about 0.004 in. to matrix mesh 86, using a spatula or flat plastic knife, and allowing the mixture to air cure at room temperature.

The volume resistivity of piezoresistive pad 83 of shear force sensor element 80 can be varied to a desired cured value by varying the amount of carbon black added to the liquid rubber, and monitoring the resistivity of the liquid mixture as those two components are being mixed together. The present inventor has found that a suitable range of volume resistivities for piezoresistive pad 83 is about 5 ohm-cm to 100,000 ohm-cm for measurement of shear forces in the approximate range of 0–5 psi, and 100–300,000 ohm-cm for measurement of shear forces in the approximate range of 5–30 psi.

Figure 5B:
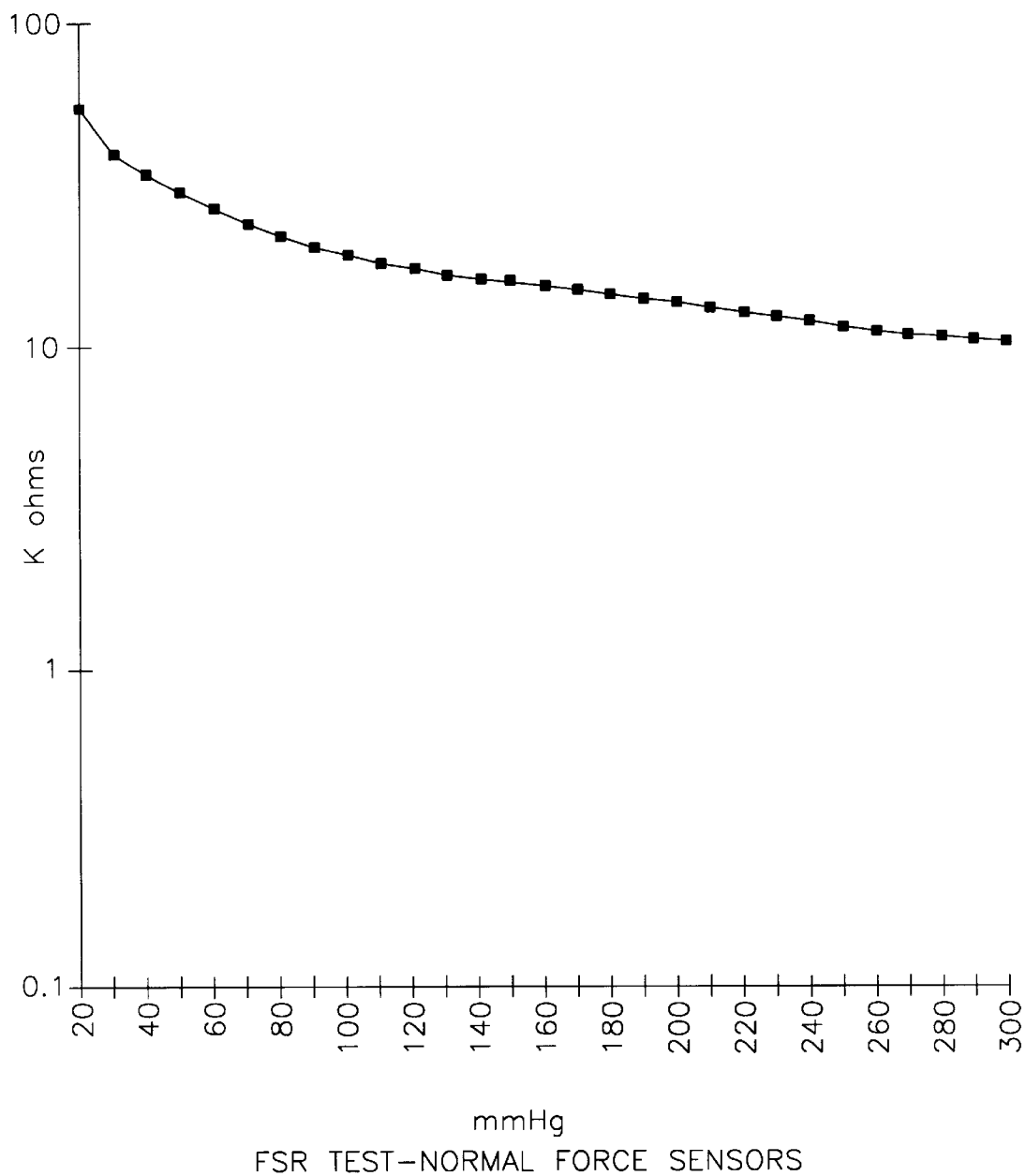
FIG. 5B is a graph of resistance versus shear force for the sensor element of FIG. 15.

A suitable material for conductive strips 81 and 82 of shear force sensor 80 is a conductive fabric consisting of nickel/copper coated polyester taffeta and marketed under the brand name FLECTRON by Monsanto, The Chemical Group, 800 N. Lindberg, St. Louis, Mo. This material has a thickness of 3.8 to 4 mils, is flexible and drapable, and has a surface resistivity of less than 0.05 ohms per square. Preferably, each conductive strip 81 and 82 has slits cut perpendicularly inward from opposite longitudinal edges of the strip, to allow stretching of the strip in a direction parallel to its longitudinal axis. As shown in FIG. 13, slits 88 are located in laterally spaced apart pairs, one pair being spaced laterally outwards from each side of a pair of opposed piezoresistive pads 83. FIG. 5B illustrates a typical variation of the electrical resistance between lower and electrode conductor strips 81 and 82, of sensor element 80, as a function of shear force directed normally to contacting surfaces 84 of piezoresistive pads 83 of the sensor element, i.e., in the X or Y direction in FIG. 15.

Figure 18B:
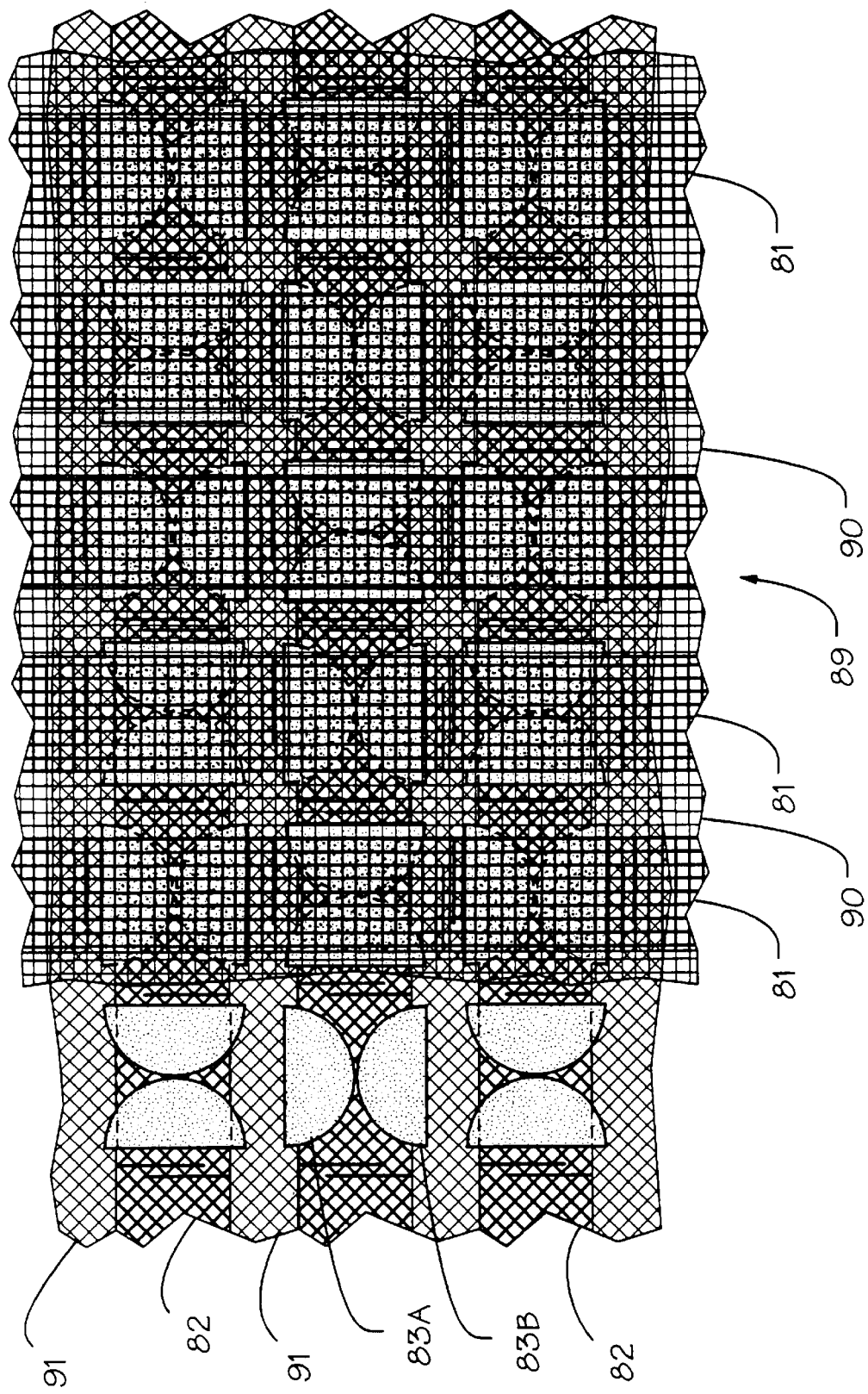
FIG. 18B is an upper plan-view of a rectangular array of shear force sensors of the type shown in FIG. 15.

FIG. 18B illustrates a planar array 89 of shear force sensor elements 80 in which a plurality of column conductive strips 81 and row conductive strips 82 form a rectangular matrix of shear force sensor elements. In regions exterior to piezoresistive pads 83 of sensor elements 80, column and row conductive strips 81 and 82 may be electrically isolated from one another, to prevent short circuiting, by means of thin column and row insulating strips 90 and 91, respectively. The insulating strips may be made of any suitable electrically insulating material, such as nylon. Preferably, however, insulating strips 90 and 91 are integral with the non-conductive fabric substrates of conductive strips 81 and 82. In this case, conductive material on the Flectron fabric is stripped away from insulating areas 90 and 91 by photo-etching using a ferrous chloride solution.

In the embodiment 89 of a planar shear force sensor array shown in FIG. 18B, the sensitive or "S" axis of each shear force sensor element 80 is oriented perpendicularly to the S axis of each of its neighbors. This arrangement of shear force sensor array 89 affords a capability for mapping shear forces in two orthogonal, X and Y directions parallel to the plane of the sensors.

After mesh fabric matrix sheets 86 have been impregnated with piezoresistive substance 87 and the latter allowed to cure, the piezoresistive pads 83 thus formed are positioned between upper and lower conductive strips 82 and 81. In the preferred embodiment, a rectangular array of spaced apart contacting pairs of piezoresistive pads 83A and 83B is formed on a pair of lower and upper fabric matrix sheets 86A and 86B, as for example, by screen printing piezoresistive ink onto the matrix sheets. The matrix sheets are then positioned between upper and lower column and row laminations having on the inner facing surfaces thereof spaced apart column and row electrode conducting strips, of the type illustrated in FIGS. 7A–7D and described above. Row and column laminations are then sealed to one another to encapsulate matrix sheets 86A and 86B and pairs of piezoresistive shear force sensing pads 83A and 83B, in a manner similar to that described above for normal force sensor 40.

Figure 20A:
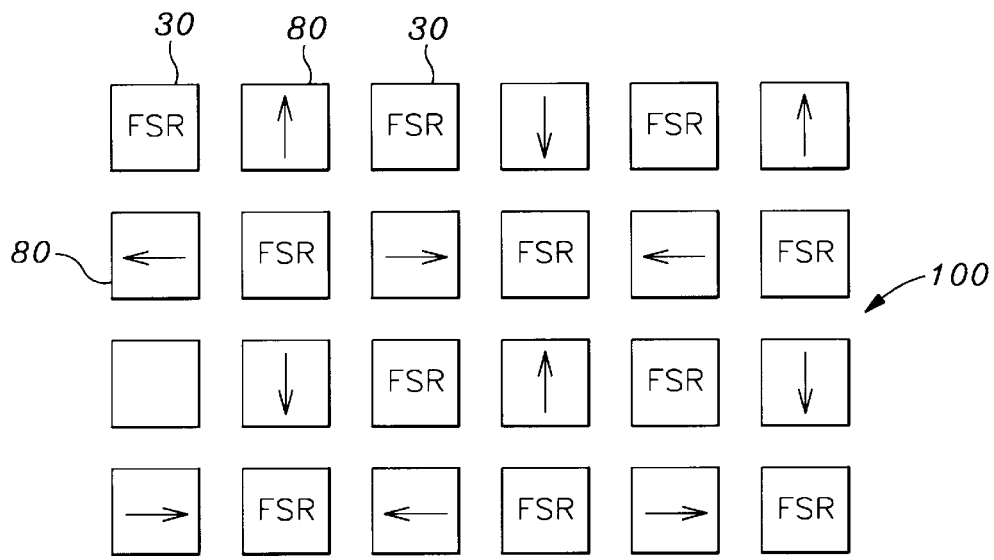
FIG. 20A is a schematic diagram showing the relative orientation of sensors comprising the array of FIG. 19.
Figure 20B:
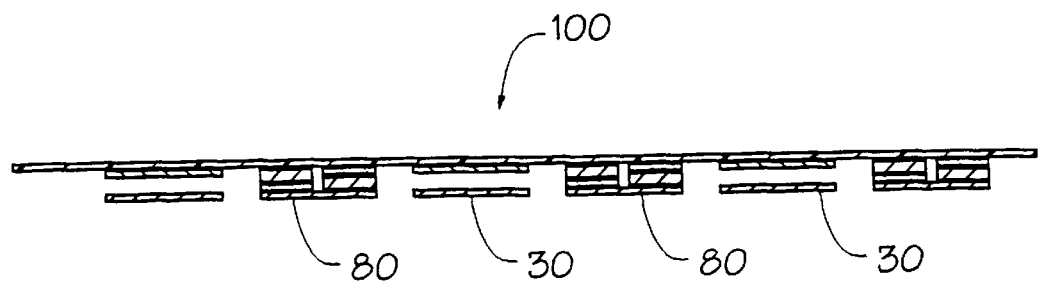
FIG. 20B is a fragmentary transverse sectional view of the array of FIG. 19, taken along line 20B—20B.
Figure 19:
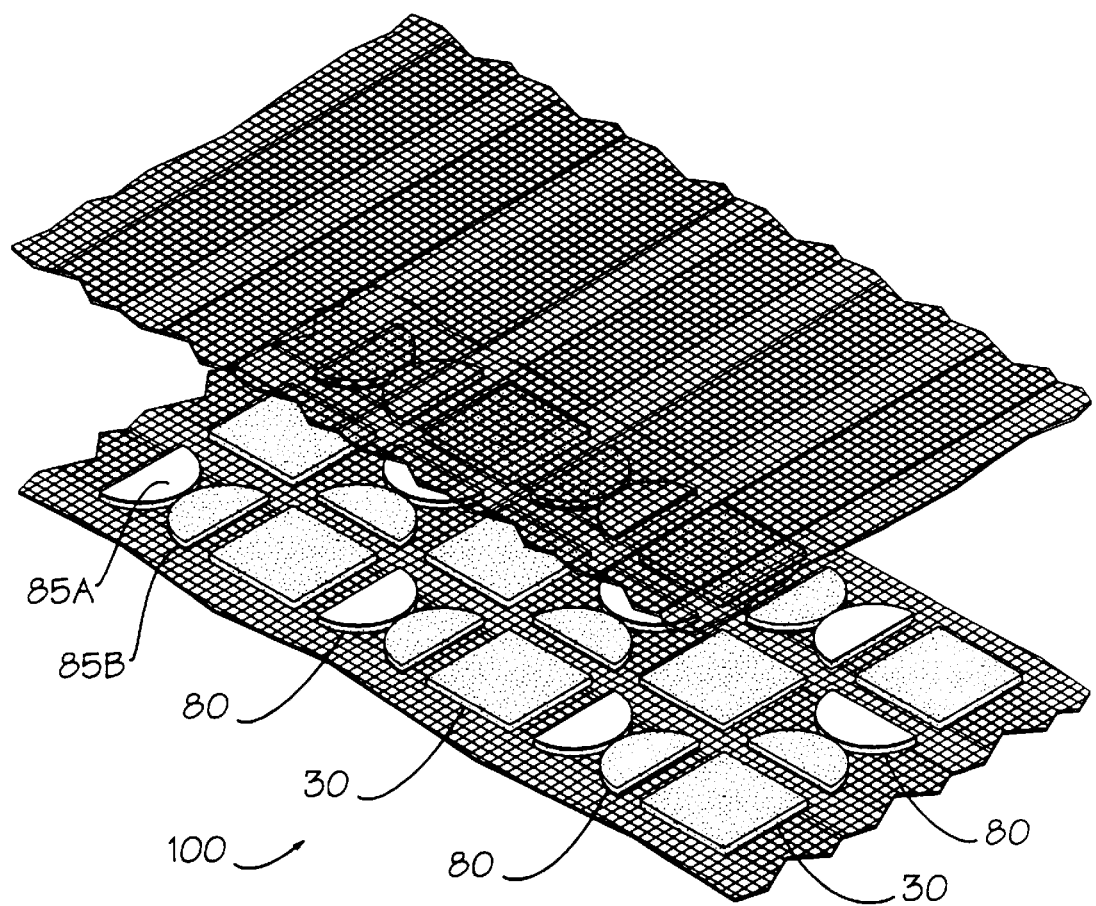
FIG. 19 is a fragmentary exploded view of a sensor array comprised of normal force sensors of the type shown in FIG. 1, alternating with shear force sensors of the type shown in FIG. 15, and showing a portion of an upper lamination thereof peeled away to reveal the sensors.

FIGS. 19–20E illustrate a modification 100 of a foot pressure sensor array 40 according to the present invention, in which shear force sensor elements similar to elements 80 described above, are interspersed with normal force sensor elements similar to elements 30 described above.

Figure 20C:
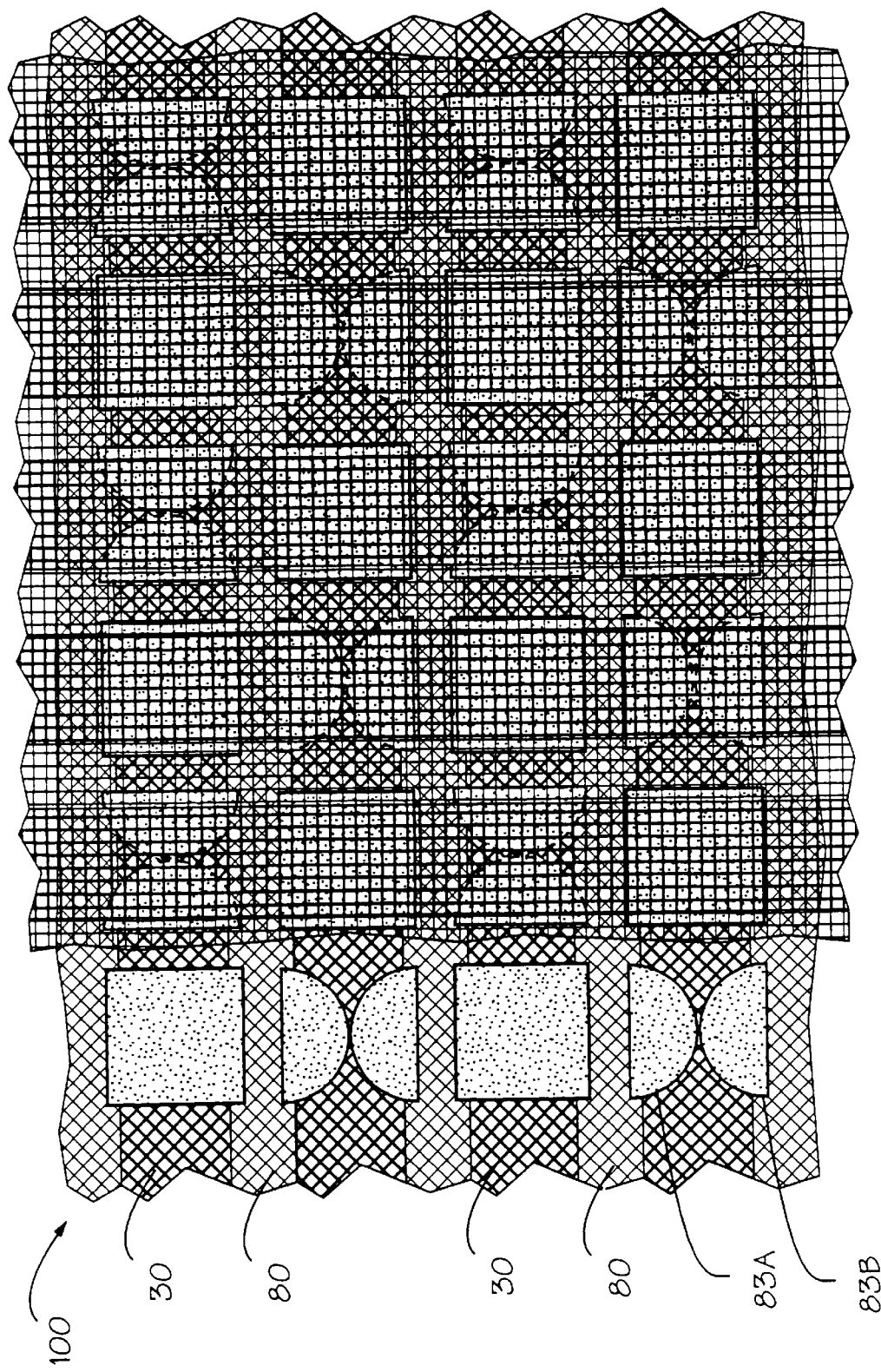
FIG. 20C is a fragmentary lower plan-view of the sensor array of FIG. 19.

As may be seen best by referring to FIGS. 19 and 20C, foot pressure/shear sensor array 100 includes a rectangular array of generally rectangular plan-view normal force sensor elements 30, in which each normal force sensor is bordered on either lateral side by a pair of shear force sensor elements 80, with their sensitive axes S aligned in a first horizontal direction, and on either longitudinal side by a pair of shear force sensors having their sensitive axes S aligned in a second horizontal direction perpendicular to sensitive axes of the first pair of shear sensor elements. Aside from the interspersing of shear force sensor elements 80 with normal force sensor elements 30, the construction of foot pressure/shear sensor array 100 is substantially similar to that of foot pressure sensor array 40. Thus, sensor array 100 has elements numbered 101–119 that are exactly analogous in structure and function to elements 41–59 of the pressure sensor array 40. Accordingly, a complete understanding of the structure and function of elements 101–119 may be obtained by referring to the previous description of elements 41 through 59.

Thus, as shown in FIG. 20E, foot pressure/shear force sensor 100 includes a lower, row conductive strip lamination 106 having row conductive strips 112. As may be seen best by referring to FIG. 20D, sensor array 100 also includes an upper, column lamination 101 having column conductive strips 111 that overlie piezoresistive normal force sensor elements 30, the latter alternating in a rectangular array with shear force sensor elements 80.

In the combined shear/normal force sensor array 100 depicted in FIGS. 19 and 20C, normal force sensor elements 30 are preferably fabricated by impregnating a mesh fabric matrix sheet 34 with square areas of piezoresistive material 35, the squares being arranged in parallel diagonal rows, such as rows 92 in FIG. 19. As shown in FIGS. 19 and 20C, diagonal rows 92 of normal force sensor elements 30 alternate with diagonal rows 93 of shear force sensor elements 80. As is also shown in FIGS. 19 and 20C, the sensitive axes S of shear force sensor elements 80 in each diagonal row alternate between the X and Y directions.

One method of fabricating array 100 of normal force sensors 30 alternating with shear force sensors 80 consists of perforating normal force sensor array matrix sheet 34 with square apertures 120 aligned with diagonal rows 93 of shear force sensor elements 80. Preferably, apertures 120 are slightly larger than shear sensor elements 80. With this arrangement, perforated normal force matrix sheet 34 may be vertically aligned with a pair of matrix sheets 86A and 86B on which are formed the pairs 83A and 83B of piezoresistive pads of shear force sensor elements 80. Thus configured, normal force matrix mesh sheet 34 could be located above or below shear force matrix sheet pair 86A and 86B. Preferably, however, normal force matrix mesh sheet 34 is located between lower and upper shear force matrix sheets 86A and 86B.

Figure 21:
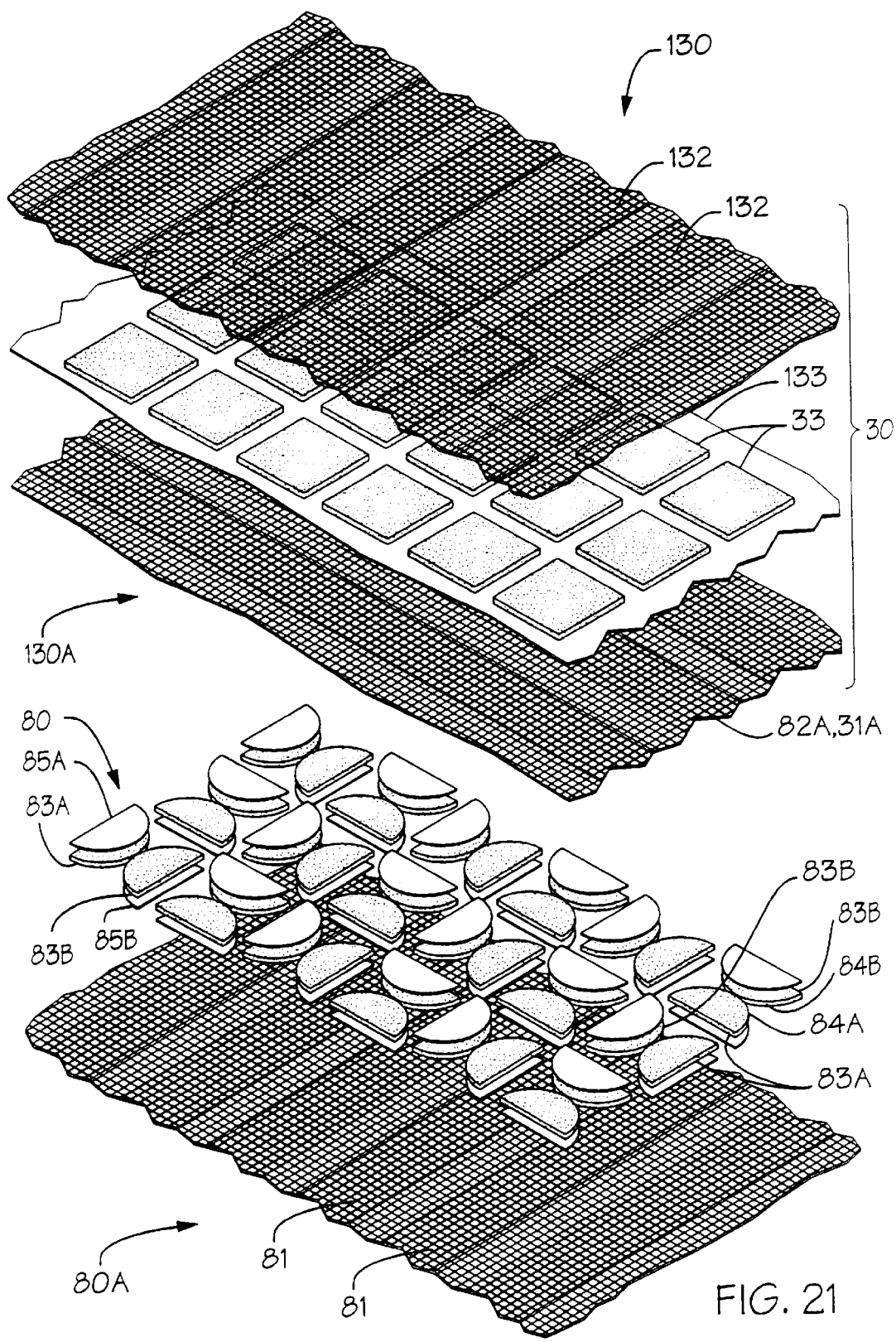
FIG. 21 is an exploded upper perspective view of an array of combined (stacked) shear and normal sensor elements according to the present invention.

FIG. 21 illustrates an array 130 of combined shear/normal force sensor elements according to the present invention. The embodiment of the invention shown in FIGS. 19 and 20 includes normal force sensor elements 140 that are substantially similar in structure and function to normal force sensor element 30 shown in FIGS. 1–4 and described above, stacked above or below shear force sensor elements 150 which are substantially similar in structure and function to shear force element 80 shown in FIGS. 16 and 18 and described above. Thus, as shown in FIG. 21, stacked shear/normal force sensor array 130 includes a planar array 130A of shear force sensor elements 80 which have a common first, lower lamination 80A having on the upper surface thereof inner column or row conductive strips 81 and, a second, upper lamination 82A having on the lower surface thereof row or column conductive strips 82. As shown in FIG. 21, each shear force sensor element 80 of array 130A includes a pair of elastomeric piezoresistive pads 83A and 83B located between conductive strips 81 and 82. Piezoresistive pads 83A and 83B have surfaces 84A and 84B, respectively, which tangentially contact one another. Pad 83A is in electrically conductive contact with lower conductive strip 81, and pad 83B is in electrically conductive contact with upper conductive strip 82. Thus, when contacting surfaces 84A and 84B of pads 83A and 83B are urged into more intimate contact in response to shear forces directed normal to their tangent contact plane, the electrical resistance between the conductive strips is reduced, a phenomenon which may be referred to as tangential or surface piezoresistivity. As shown in FIG. 21, shear force sensor element pads 83A and 83B preferably are arranged in array 130A so that the tangent planes of adjacent shear force sensor elements 80 are perpendicular to one another. This arrangement permits measurement resolution of shear forces in any direction parallel to array 130A into two mutually orthogonal components.

To electrically isolate lower piezoresistive pads 83A, which are conductively coupled to lower conductive strips 81, from upper conductive strips 82, thin, flexible insulating strips 85A are positioned between that portion of the lower surface of the upper conductive strip that overlies pads 83A, and the upper surface of the pads. In the preferred embodiment, insulating strips 85A are made of a slippery material such as TEFLON, the lower surface of the sheet thereby facilitating sliding lateral motion of lower piezoresistive pad 83A relative to upper conductive strip 82, in response to lateral or shear forces exerted on lower strip 81 relative to upper strip 22. Similarly, slippery insulating strips 85B are located between the upper surface of lower conductive strips 81 and upper piezoresistive pad 83B, to electrically isolate upper piezoresistive pad 83B from lower conductive strip 81, while permitting slidable motion of the pads with respect to the strip. In the preferred embodiment, each piezoresistive pad 83A and 83B is fabricated integrally with conductive strip 81 or 82 was described above with reference to FIGS. 15, 16 and 18A.

Stacked shear/normal force sensor element array 130 also includes normal force sensor elements 30 which have a common first, lower lamination 31A having on the upper surface thereof column or row conductive strips 31. Lower conductive strips 31 may be adhered to the upper surface of an insulating sheet positioned over shear force array upper lamination 82A. Alternatively, lamination 82A may be a double-sided printed circuit, the lower surfaces of the insulating sheet having formed thereon traces comprising the upper, column conductive strips 82 of shear force sensor elements 80, and having formed on the upper surface thereof traces comprising the lower, row conductive traces 31 of normal force sensor elements 30. However, in the most preferred embodiment, lamination 82A is fabricated with conductive strips extending through the thickness dimension of the lamination, according to the novel construction employing etched, plated fabric described above. With this arrangement, upper, column conductive strips 82 of shear force sensor elements 80 may be common with lower column conductive strips 31 of normal force sensor elements 30.

Sensor array 130 also includes an upper lamination 132A having on the lower surface thereof a plurality of column or row conductive strips 132, that are disposed perpendicularly to conductive strips 31. A piezoresistive layer 133 is positioned between column and row conductive strips 31 and 132, and functions in response to normal forces exerted thereon as has been previously described.

Thus constructed, combined shear/normal force sensor elements 130 can be arranged in a rectangular array similar to that shown in FIGS. 7A–7D. However, in this case, one or two additional lead-out tongues 144A, 144B must be brought out from the array, as indicated by the dotted lines in FIG. 7A. The additional lead-out tongues are required to accommodate the two additional layers of conductors required for the stacked configuration of shear and normal force sensors.

In the arrangement of stacked shear/normal force sensor element 130 shown in FIGS. 19 and 20, normal force sensor element 30 is positioned above shear force sensor element 80. This order could of course be reversed.

Figure 24:
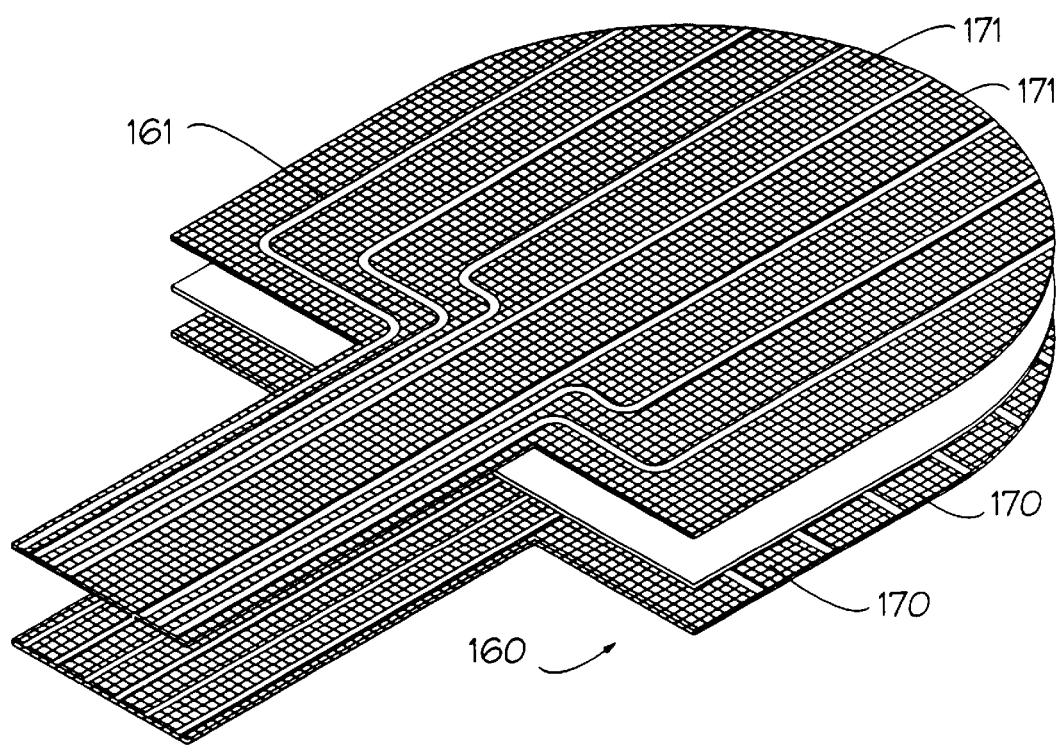
FIG. 24 is an upper perspective view of a normal force sensor array comprising normal force sensors of the type shown in FIG. 1, the array being adapted for measuring normal forces exerted on the hoof of a horse.
Figure 25B:
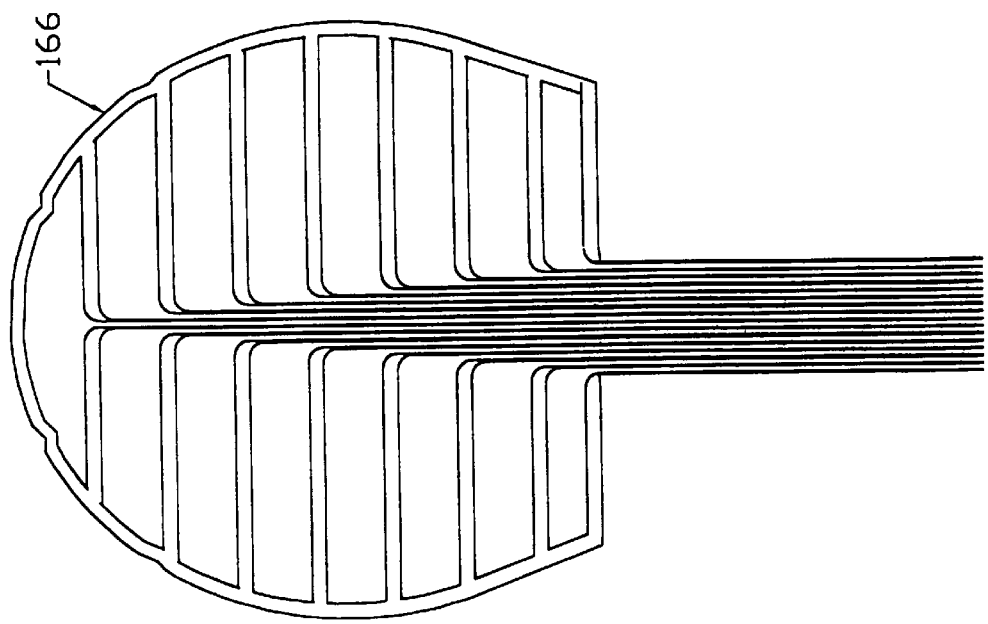
FIG. 25B is a lower plan-view of the upper, column lamination of the array of FIG. 23.
Figure 25A:
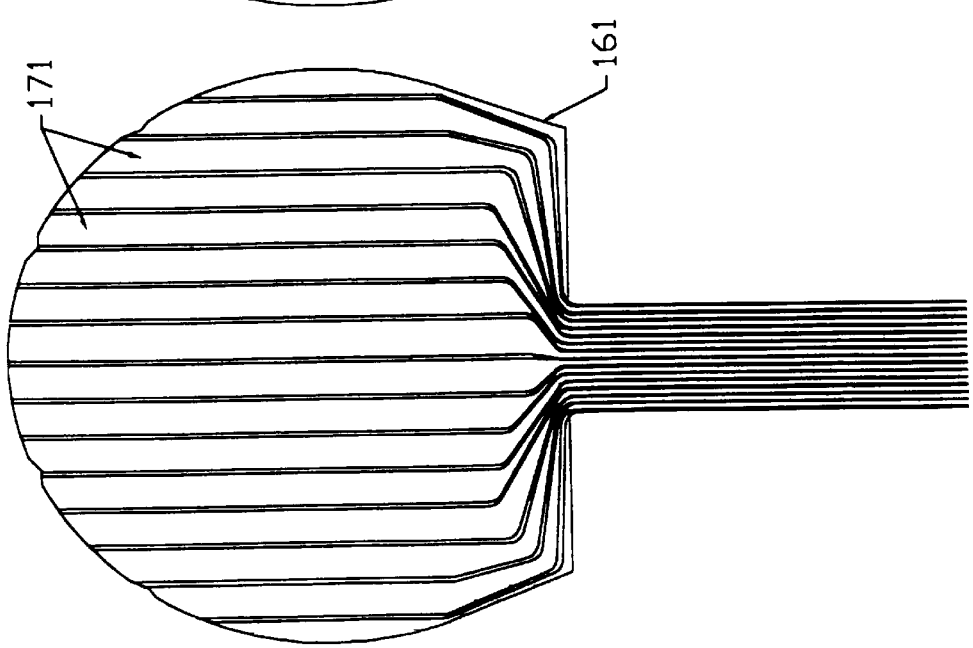
FIG. 25A is a lower plan-view of the sensor array of FIG. 23.

FIGS. 24–25A illustrate a normal force sensor array 160 that is particularly well adapted for measuring normal forces or pressures exerted on the bottom surfaces of horses' hooves, by horseshoes, for example. Hoof pressure sensor array 160 employs normal force sensor elements 170 substantially similar in structure and function to the normal force sensor elements 30 shown in FIGS. 1–4 and described above, with the sensor elements arranged in a rectangular array similar to array 37 shown in FIG. 6. Also, hoof pressure sensor array 160 is substantially similar in structure and function to foot pressure sensor array 40. Thus, hoof pressure sensor array 160 has elements 161–187 substantially similar in structure and function to elements 41–67 of foot pressure sensor array. Since the structure and function of the latter elements were described in detail above, a thorough understanding of the corresponding elements of hoof pressure sensor array 160 may be obtained by referring to that description.

As may be seen by referring to FIGS. 24–25A, some of the construction details of hoof pressure sensor 160 differ somewhat from those of foot pressure sensor 40. Thus, as shown in FIGS. 23–24B, the laminations comprising hoof pressure sensor 160 have in plan-view a shape approximating a horse's hoof print rather than a human foot print. Also, the piezoresistive substance 186 used to impregnate mesh fabric matrix sheet 184 differs from piezoresistive material 66 used in foot pressure sensor array 160 by having a higher volume resistivity of about 500,000 ohm-cm versus 100,000 ohm-cm, thus resulting in a piezoresistive layer 183 that has greater linearity and minimum hysteresis for the larger pressure ranges of 1,000 to 6,000 psi resulting from the larger weight of horses.

It will be recalled that a planar foot pressure measuring and mapping apparatus 68 illustrated in FIG. 12 was described above. That apparatus includes a foot pressure sensor array 40, which may be replaced by hoof pressure sensor array 160, thus enabling apparatus 68 to measure and map hoof pressures rather than foot pressures.

Figure 26:
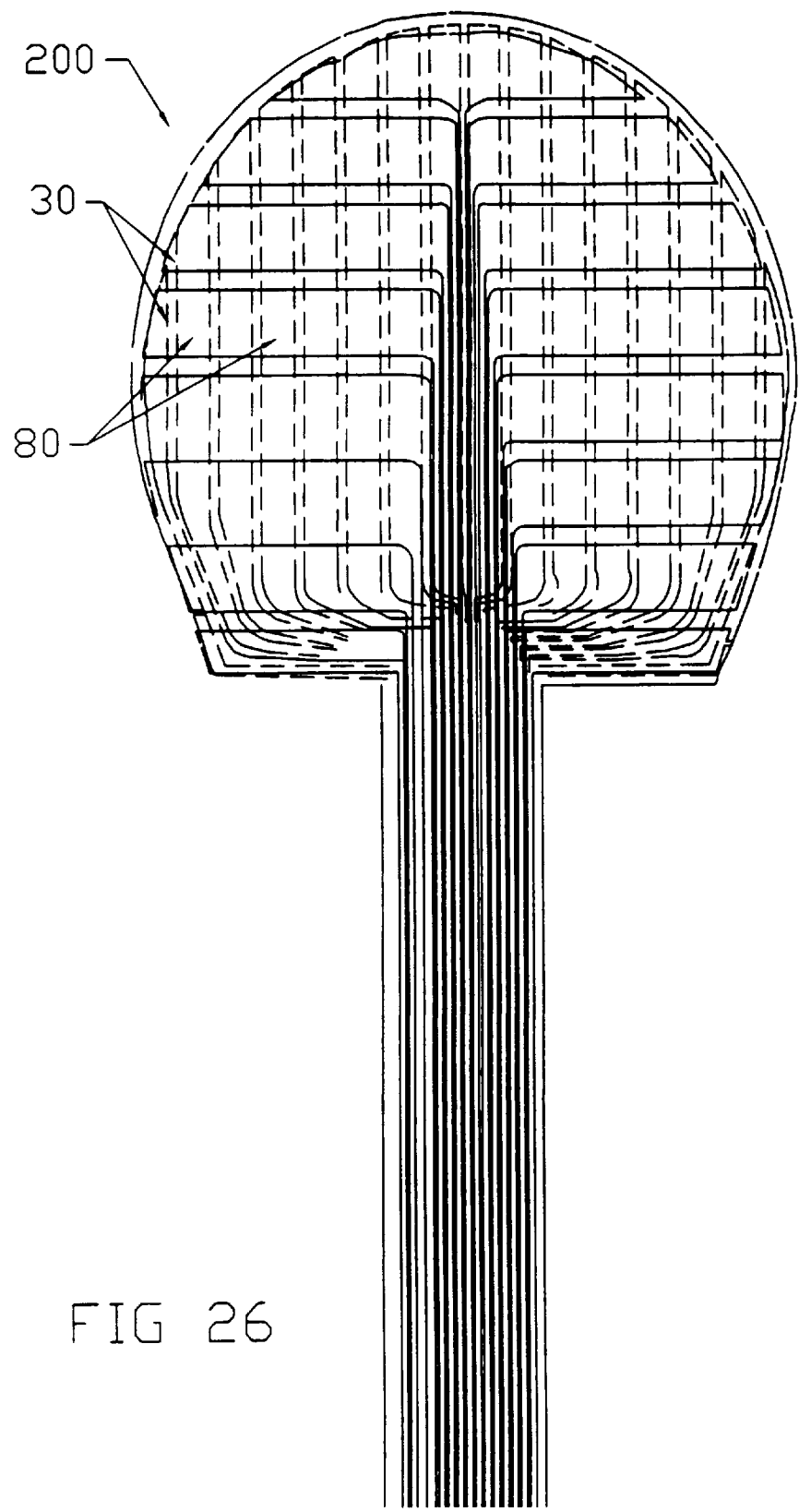
FIG. 26 is an upper perspective view of another sensor array adapted for measuring shear forces as well as normal forces exerted on the hoof of a horse, the array comprising normal force sensors of the type shown in FIG. 1, alternating with shear force sensors of the type shown in FIG. 15.

FIG. 26 is a lower plan-view of a modification 200 of a hoof pressure sensor array 160 according to the present invention, in which shear force elements similar to elements 80 described above, are interspersed with normal force sensor elements similar to elements 30 described above. Modified hoof pressure/shear sensor array 200 is substantially similar in structure and function to modified foot pressure/shear sensor array 100 illustrated in FIGS. 17–18B and described above. Thus, hoof pressure/shear force sensor array 200 has elements 201–219 substantially similar in structure and function to elements 101–119 of foot pressure/ shear force sensor array 100. Since the structure and function of the latter elements were described in detail above, a thorough understanding of the corresponding elements of hoof pressure/shear force sensor array 200 may be obtained by referring to that description.

As was described above, stacked, combined shear/normal force sensor elements 130 can be substituted for alternating normal force sensor elements 30 and shear forced elements 80 in foot pressure/shear force sensor array 100. This substitution could of course also be made in hoof pressure/ shear force sensor array 200.

FIGS. 27–33 illustrate a sock 220 that may be fitted with any of the sensor arrays 40, 100, 160, or 200 described above. The construction of sock 200 is as follows: The sock is made up of three conductive tubular laminations, an inner tube 221 with longitudinal conductor strips, a center tube 222 bearing piezoresistive material and an outer tube 223 containing lateral or circumferentially disposed conductor strips which wrap around the sock. A fourth, lead-out layer/strip 224 is provided to make electrical contact with each of the lateral conductor strips.

In the preferred embodiment of force sensing and mapping sock 220, each of tubes comprising the sock is made of a mesh fabric material. Thus, inner, column conductor lamination 221, row conductor lamination 223, and row lead-out lamination 224 are preferably made of a conductive mesh fabric such as the Flectron material described above.

As shown in FIG. 31, inner column conductor tubular lamination 221 comprises a tubular Flectron sock base or matrix 231, having etched through the thickness dimension thereof, longitudinally disposed insulating paths 232 defining longitudinally disposed, laterally spaced apart column conductors 233 terminating at the opening of the sock in lead-out traces 234.

Figure 32:
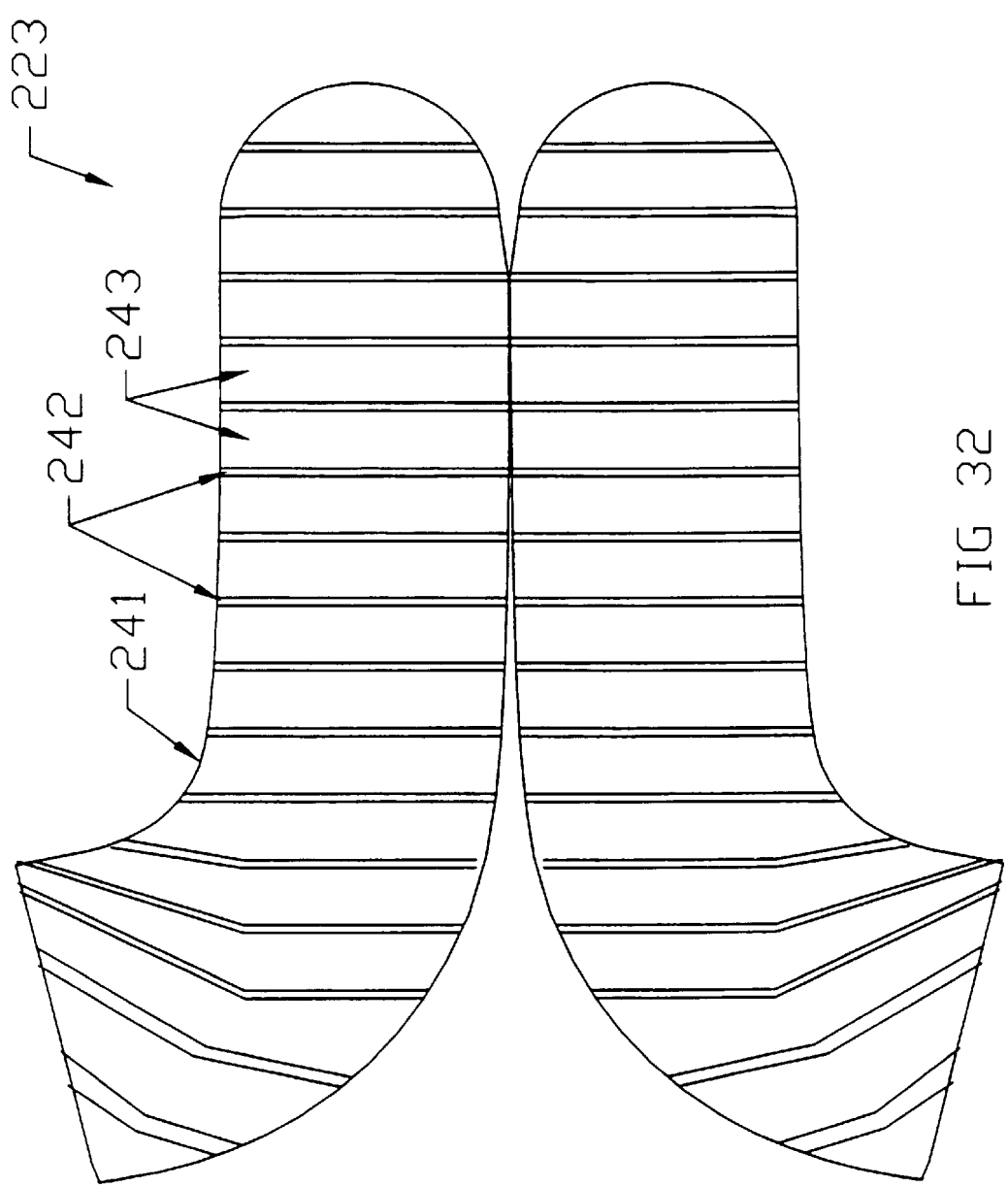
FIG. 32 is a cut and folded-flat view of an outer, row conductor tube comprising part of the sock shown in FIG. 27.

As shown in FIG. 32, outer, row conductor tubular lamination 223 comprises a tubular Flextron sock base or matrix 241 having etched through the thickness dimension thereof circumferentially disposed insulating paths 242 defining circumferentially disposed, longitudinally spaced apart row conductors 243.

Figure 33:
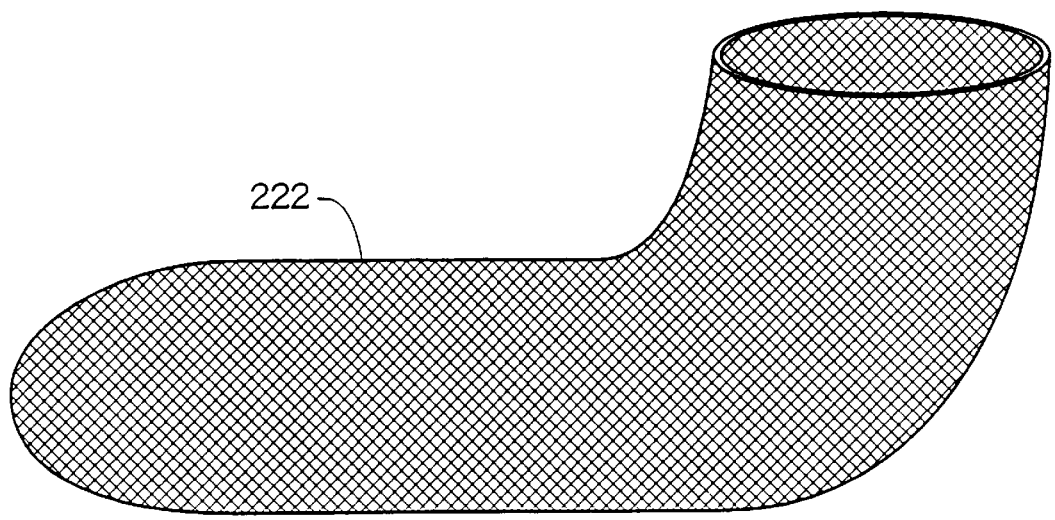
FIG. 33 is a fragmentary perspective view of a piezoresistive tube comprising part of the sock of FIG. 27.
Figure 29:
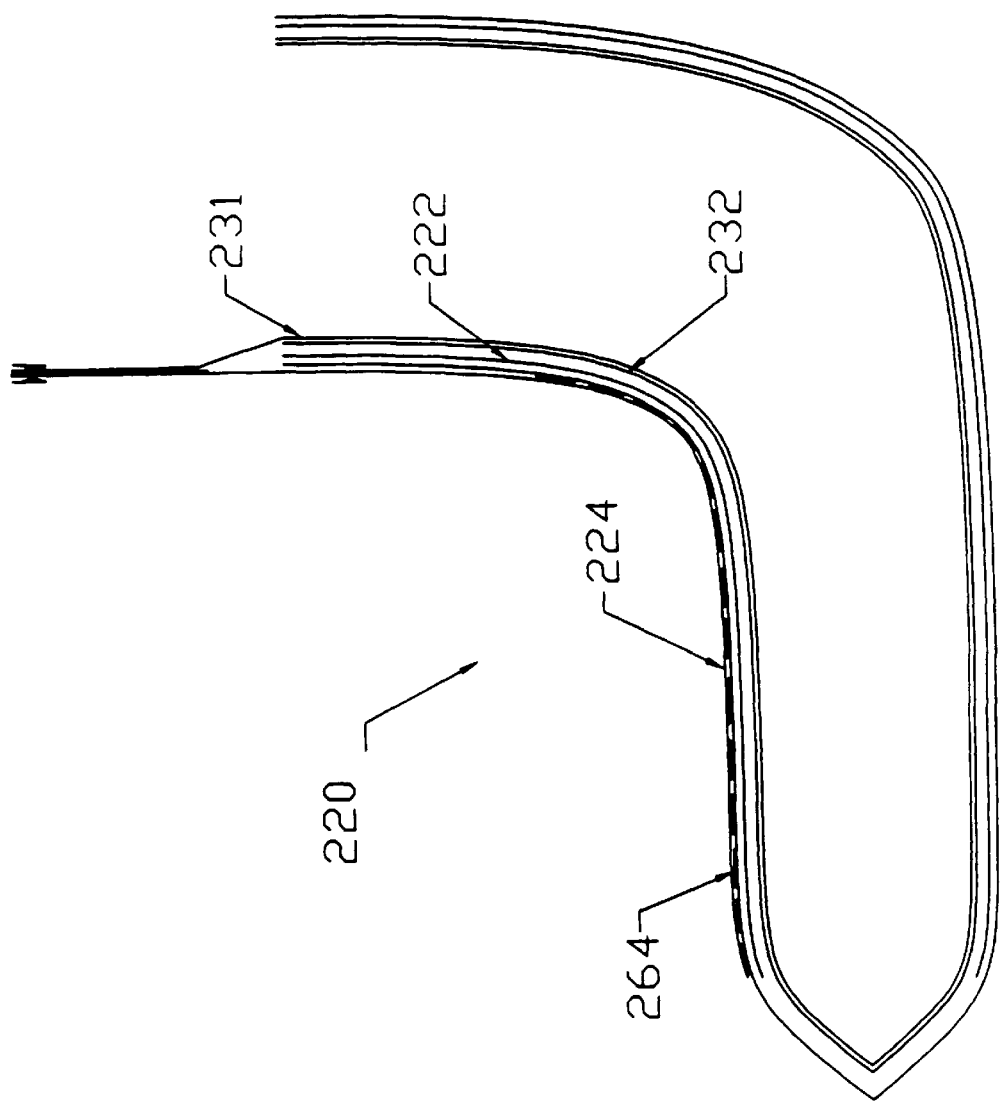
FIG. 29 is a longitudinal sectional view of the sock shown in FIG. 27.

As shown in FIGS. 29 and 33, piezoresistive tubular lamination 222 comprises a tubular sock made of a non-conducting mesh fabric impregnated with piezoresistive material, in a manner previously described.

Figure 27:
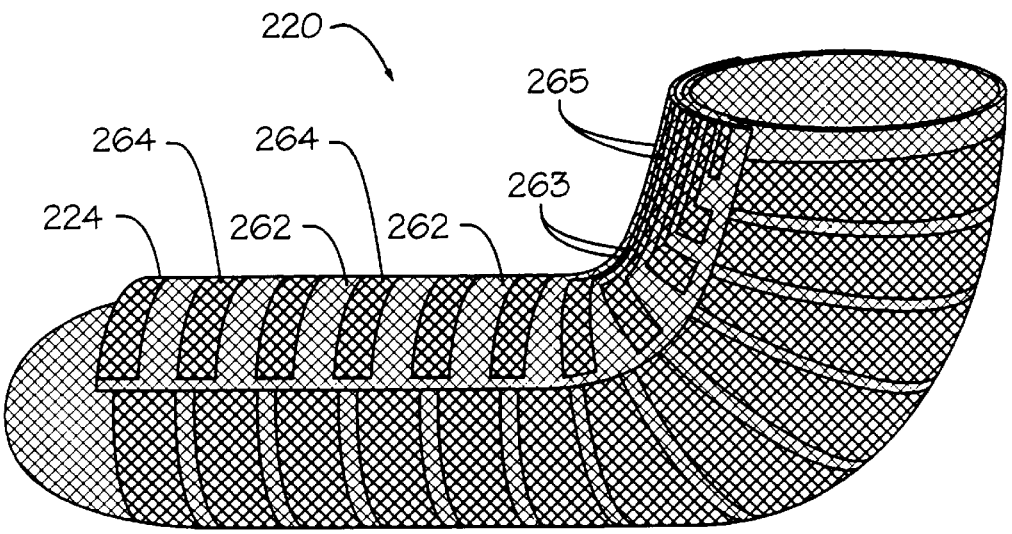
FIG. 27 is a perspective view of a sock incorporating force sensors according to the present invention.
Figure 28:
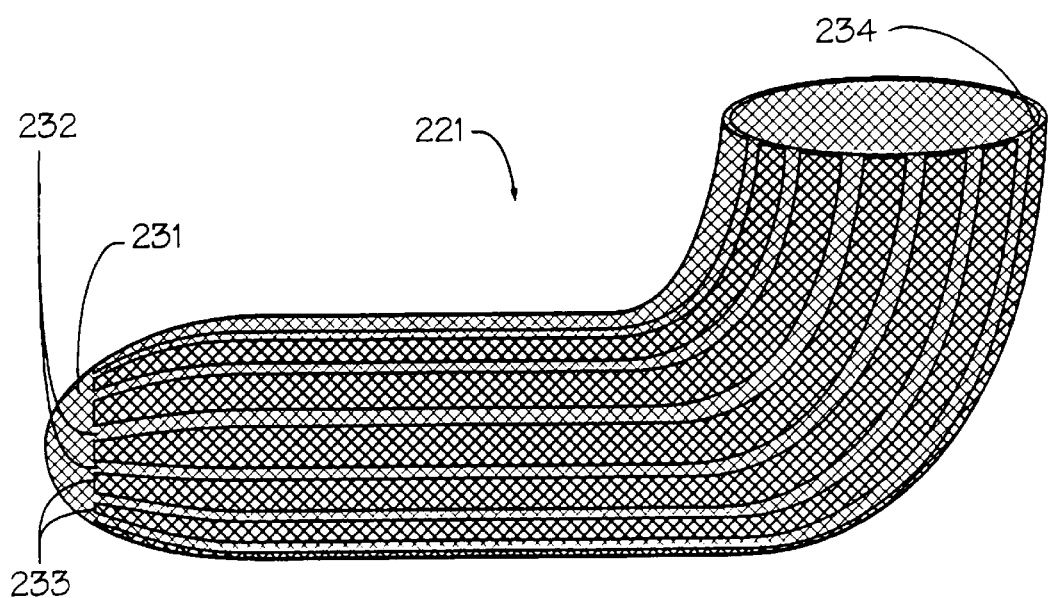
FIG. 28 is a perspective view of an inner, column conductor tube comprising part of the sock shown in FIG. 27.

Referring now to FIGS. 27 and 29, force sensing and mapping sock 220 may be seen to include an outer tubular row lead-out tubular lamination 224. Lead-out tubular lamination 224 is made from Flextron material having etched through the thickness dimension thereof circumferentially and longitudinally disposed insulating paths 262 and 263 defining laterally disposed longitudinally flag appendages 264 connected to longitudinally disposed lead-out traces 265.

Figure 34:
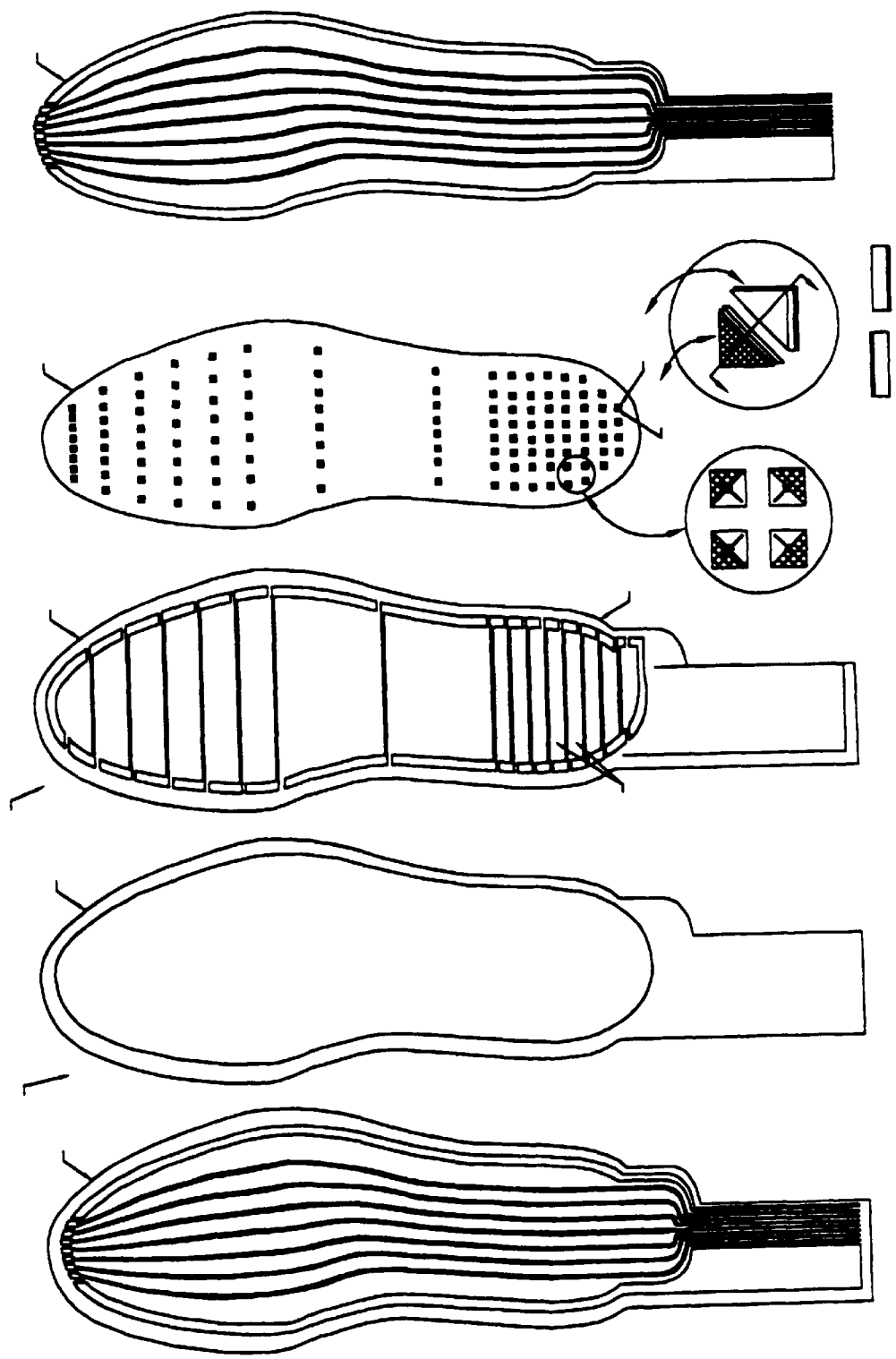
FIGS. 34A and 34E show an upper plan view of the upper lamination of an alternate embodiment of the normal force sensor shown in FIG. 20D.
FIGS. 34B–34D are upper plan views of first, second and third laminations, respectively, of the sensor of FIG. 34A.
Figure 35:
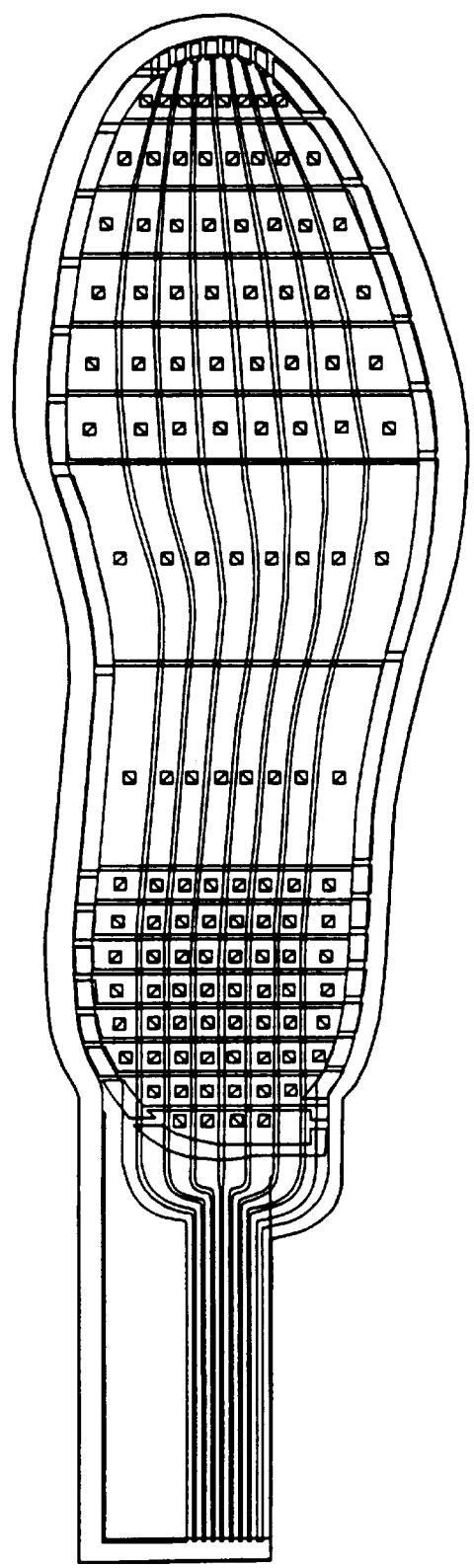
FIG. 35 is an upper plan view of the sensor of FIGS. 34A–34E.

FIGS. 34 and 35 illustrate an alternate embodiment of a force sensor array according to the present invention, which utilizes a variation of the shear force elements previously described.

As shown in FIGS. 34A–34C and 34E, alternate shear force sensor array 400 has laminations 401A, 423, 426, and 401B, substantially identical in structure and function to those previously described with reference to FIGS. 12, 20D and 20E. However, in the embodiment 400 of a force sensor array, shear force sensors 480 are arrayed in a separate layer using the horizontal conductive elements from a normal force sensor as a first conductive array on a first side of the shear force sensor elements, and a second layer of vertical conductive elements as a second, perpendicular conductive array for the second side of the shear force sensor elements.

As shown in FIG. 34D, each shear force sensor element 480 includes a pair of mating right-triangularly-shaped piezoresistive pads 483A and 483D having mating hypotenuse surfaces 484A and 484B, the two pads thus defining a square shape. Each shear force sensor element pad 483A, 483B has a teflon coating or sheet 485A, and 485B adhered to one side thereof. The other side of each pad is in electrically conductive contact with a row or column conductor strip. Shear forces imposed on the pads 483A and 483B urge the pads into more or less intimate contact, thus varying the electrical resistance between the pads.

With pads 483A and 483B slidably movable towards one another, without any pre-load forcing the pads together, sensor element 480 is more sensitive to forces tending to urge the pads into more intimate contact than to forces tending to separate the pads. This somewhat non-bilateral characteristic may also be present in the basic embodiment of shear force sensor element according to the present invention and described above. Thus, in the absence of a pre-load force tending to bias pads 483A and 483B together, it is preferable to employ diagonally opposed pairs of sensor elements 480A and 480B as shown in FIG. 34, assuring adequate bilateral sensitivity of the sensor element pad array, as shown in FIG. 35.

Figure 36:
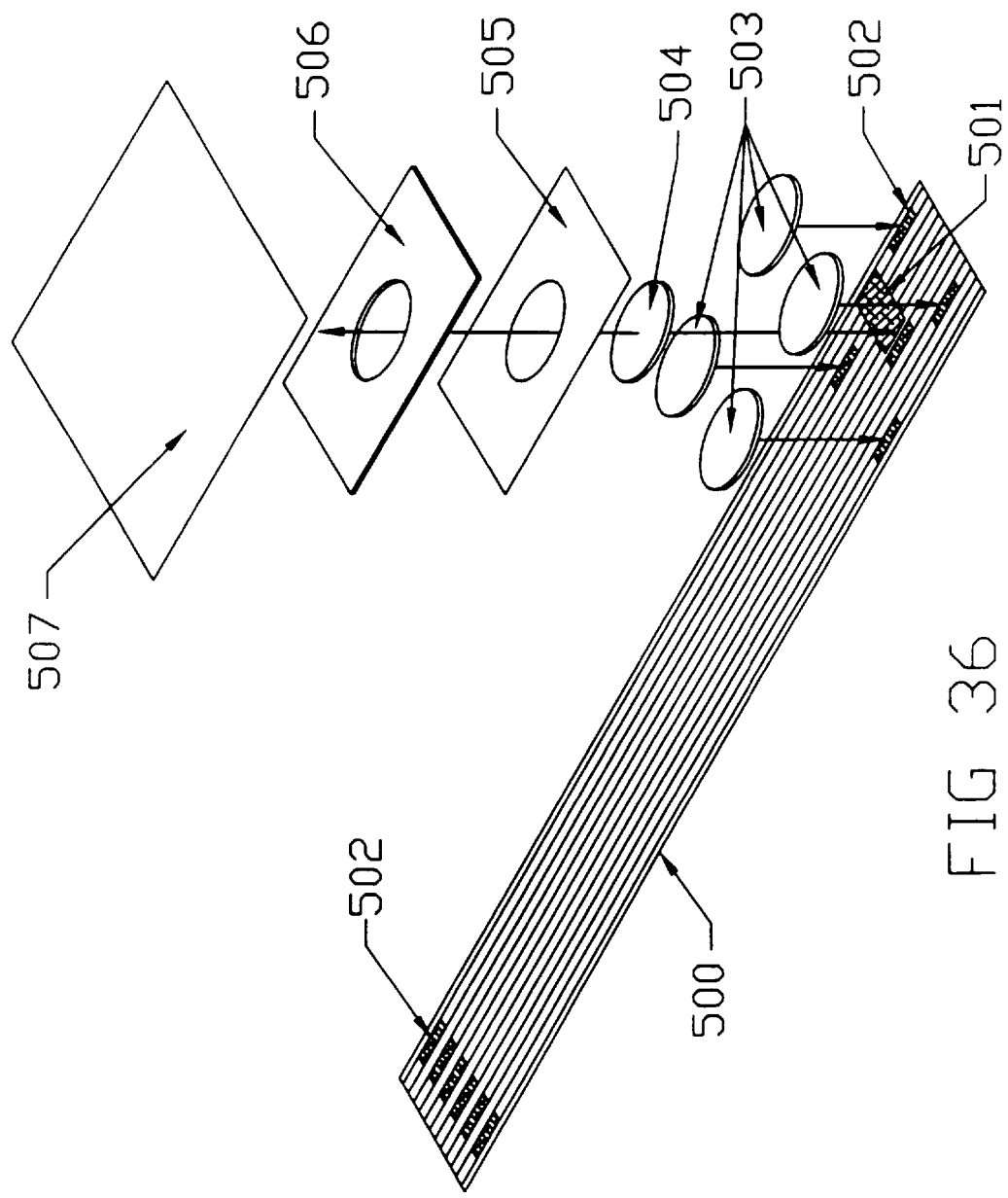
FIG. 36 is an upper perspective view of another modification of the shear and normal force sensor of FIG. 20B.

In another shear force sensor array embodiment shown in FIG. 36, circularly-shaped, piezoresistive pads 503 are placed on multi-conductor flat cable 500. Spots 502 are bared on (hc flat cable to coincide with placement of the four circular pads 503 of the shear sensor 499. This allows the pads to contact the flat cable and these are adhered to the cable using a conductive adhesive. There are also two additional bared areas which make up the normal force sensor element. One of the central normal force elements acts as the common electrical contact and the other is covered with a layer of piezoresistive normal force sensing material 501. A central round aluminum element 504 comes into contact with the central piezoresistive layer 501, allowing it to act as the normal force sensing element. Element 504 also tangentially contacts pads 503 and serves as the common element for those pads. The tops of the four pads 503 are covered with Teflon sheet 505 to reduce friction with the plastic cover plate 506. The whole assembly is covered with latex rubber 507 to ensure a good friction to surrounding surfaces.

What is claimed is:

1. A device for measuring forces exerted on a discrete location of a surface, said device comprising at least a first normal force sensing element (30), said element containing a piezoresistive material defined as having a hulk electrical resistance that varies in a predetermined way with normal forces exerted thereon, said piezoresistive material being in the form of a resilient pad (33) sandwiched between a pair of first and second conductor strip laminations comprising thin, flexible insulating sheets having formed on the inner facing surfaces thereof at least one row (32) and at least one column (31) conductor strip, respectively, said row and column conductor strips being in electrically conductive contact with opposite sides of said piezoresistive pad, at least one of said resilient pads, said row and said column conductor strips comprising a woven mesh fabric (34) impregnated with electrically conductive material, whereby the electrical resistance between a selected row and column conductor intersection defining a particular region normally aligned with said pads in a predetermined function of the normal force exerted on said region.

2. The device of claim 1 wherein at least one of said row and column conductor strips is further defined as being made of an electrically conductive, woven fabric that is flexible and drapable.

3. The device of claim 1 wherein at least one of said conductor strips is further defined as having formed therein at least one transversely disposed slit (36) spaced apart from said piezoresistive pad (33), said slit facilitating longitudinal stretching of said strip.

4. The device of claim 1 further comprising at least one additional one of said resilient pads (33), each of said first and additional pads being spaced apart and electrically isolated from one another and comprising together a planar two dimensional array (37) of said force sensing elements.

5. The device of claim 4 wherein said piezoresistive pads are each further defined as comprising an insulating matrix (34) impregnated with a piezoresistive substance (35).

6. The device of claim 5 wherein said matrix (34) is further defined as being a woven mesh fabric.

7. The device of claim 6 wherein said woven mesh fabric is further defined as being flexible and drapable.

8. The device of claim 4 wherein said piezoresistive substance (35) is further defined as comprising a suspension of conductive particles in a resilient material.

9. The device of claim 8 wherein said resilient material is further defined as being an elastomer.

10. The device of claim 9 wherein said elastomer is further defined as being silicon rubber.

11. The device of claim 8 wherein said conductive particles are further defined as being composed of carbon.

12. The device of claim 4 wherein said row (32) and column (31) conductor strips extend through the thickness dimension of said first and second conductor strip laminations, whereby electrical contact is made with said inner facing row and column conductor strips in contact with said piezoresistive elements by contacting elements on the outer surfaces of said cover sheets.

13. The device of claim 12 wherein said first and second, row and column conductor strip laminations are further defined as comprising a conductive fabric sheet consisting of a non-conducting fabric mesh composed of woven strands of non-conductive fibers which are plated on the outer surfaces thereof with a conductive metallic coating, said coating being etched through the thickness dimension of said mesh to produce insulating paths (33) defining conductive strips (A,B) that extend through the thickness dimension of said mesh.

14. A device for measuring shear forces exerted on discrete locations of a surface which the apparatus is placed in contact with, said device comprising a planar two dimensional array of individual shear force sensing elements (80), each of said shear force sensing elements comprising a pair of laterally adjacent piezoresistive pads (83A, 83B) having tangentially contacting peripheral surfaces (84A, 84B), the electrical resistance between said pad pair members varying in a predetermined way with shear forces directed perpendicularly to the tangent plane and urging said contacting surfaces of said pad pair into greater or lesser conductive contact, said pairs of pads being sandwiched between a pair of first and second conductor strip laminations comprising thin, flexible electrically insulating sheets having formed on the inner facing surfaces thereof adjacent rows of spaced apart row (82) and column (81) conductor strips, respectively, said row and column conductor strips being in electrically conductive contact with a separate one of each pair of pads, whereby measurement of the electrical resistance between the pads of a selected pair of said pads is measured by applying a voltage between said selected row and column conductor strips, thereby determining shear forces exerted on said pad pair.

15. The device of claim 14 wherein at least one of said halves of a pad pair is slidably supported by an electrically non-conductive sheet (85) on the surface opposite to that surface in electrically conductive contact with said pad.

16. The device of claim 14 wherein said piezoresistive pads of said shear force sensing elements are each further defined as comprising an insulating matrix (86) impregnated with a piezoresistive substance (87).

17. The device of claim 16 wherein said piezoresistive substance is further defined as comprising a suspension of conductive particles in a resilient material.

18. The device of claim 17 wherein said resilient material is further defined as being an elastomer.

19. The device of claim 18 wherein said elastomer is further defined as being silicone rubber.

20. The device of claim 17 wherein said conductive particles are further defined as being composed of carbon.

21. The device of claim 14 wherein said row and column conductor strips extend through the thickness dimension of said first and second conductor strip laminations, whereby electrical contact may be made with said inner facing row and column conductor strips in contact with said piezoresistive pads by contact elements on the outer surfaces of said laminations.

22. The device of claim 15 wherein said first and second, row and column conductor strip laminations are further defined as comprising a conductive fabric sheet consisting of a non-conducting mesh fabric composed of woven strands of non-conductive fibers which are plated on the outer surfaces thereof with a conductive metallic coating, said coating being etched through the thickness dimension of said mesh to produce insulating paths defining conductive strips that extend through the thickness dimension of said mesh.

23. The device of claim 1 further adapted for measuring pressures exerted at various locations on the bottom of a foot in response to weight placed on the foot and comprising a thin, flexible laminated structure containing a plurality of piezoresistive pressure sensing elements arranged in a planar two-dimensional array, said laminated structure comprising a first, column conductor strip lamination including a substrate made of a thin, flexible sheet of electrically insulating material having formed on a surface thereof a plurality of longitudinally disposed, laterally spaced apart column conductor strips, a second, piezoresistive lamination comprising a thin substrate matrix supporting a thin layer of resilient piezoresistive material having an electrical resistance measured normal to said layer that varies with normal forces exerted thereon, said piezoresistive layer having a first planar surface which is in electrical contact with said column conductor strips, a third, row conductor strip lamination including a substrate made of a thin, flexible sheet of electrically insulating material having formed on an inner surface thereof a plurality of laterally disposed, longitudinally spaced apart row conductor strips in electrically conductive contact with a second planar surface of said piezoresistive layer, and means for making electrically conductive contact with a selected pair of row and column conductor strips whereby the resistance of a selected piezoresistive element defined by that portion of said piezoresistive layer between said strips may be measured, said resistance being related in a predetermined way to pressure exerted on said element.

24. The device of claim 23 wherein said row and column conductor strip laminations are further defined as having longitudinally elongated lead-out tongues supporting lead-out traces in electrically conductive contact with said respective row and column conductor strips, said tongues protruding away from the pressure sensor area defined by said piezoresistive lamination.

25. The device of claim 24 where said lead-out tongues are further defined as being vertically aligned and splayed vertically apart, thereby allowing separate edge card connectors to electrically contact separate lead-out traces on the inner facing surfaces of said tongues.

26. The device of claim 23 wherein at least one of said column and row conductor strip laminations is further defined as comprising a conductive fabric sheet consisting of a non-conducting fabric mesh composed of woven strands of non-conductive fibers which are plated on the outer surfaces thereof with a conductive metallic coating, said coating being etched through the thickness dimension of said mesh to produce insulating paths defining conductive strips that extend through the thickness dimension of said mesh.

27. The device of claim 23 wherein said column and row conductor strip laminations are further defined as comprising a conductive fabric sheet consisting of a non-conducting fabric mesh composed of woven strands of non-conductive fibers which are plated on the outer surfaces thereof with a conductive metallic coating, said coating being etched through the thickness dimension of said mesh to produce insulating paths (38) defining conductive strips (A,B) that extend through the thickness dimension of said mesh.

28. The device of claim 27 wherein said column (41) and row (46) conductor strip laminations are further defined as having longitudinally elongated lead-out tongues (44) supporting lead-out traces (43) in electrically conductive contact with said respective column and row conductor strips, said lead-out tongues protruding away from the pressure sensing area defined by said piezoresistive laminations and being vertically aligned in a parallel relationship with an insulating strip between the inner surfaces of said tongues, said lead-out traces being located on the outer surfaces of said tongues.

29. A device for measuring shear and normal forces exerted on discrete locations of a surface, said device comprising a planar array of at least one shear force sensor element as recited in claim 14, interspersed with at least one normal force sensing element (30) containing a piezoresistive material defined as having a bulk electrical resistance that varies in a predetermined way with normal forces exerted thereon, said piezoresistive material being in the form of a resilient pad (33) sandwiched between a pair of first and second conductor strip laminations comprising thin, flexible insulating sheets having formed on the inner facing surfaces thereof at least one row (32) and at least one column (31) conductor strip, respectively, said row and column conductor strips being in electrically conductive contact with opposite sides of said piezoresistive pad, at least one of said resilient pads, said row and said column conductor strips comprising a woven mesh fabric (34) impregnated with electrically conductive material, whereby the electrical resistance between a selected row and column conductor intersection defining a particular region normally aligned with said pads is a predetermined function of the normal force exerted on said region.

30. The device of claim 29 wherein said normal force sensor element and shear force sensing element are arranged in a laterally spaced apart disposition relative to one another.

31. The device of claim 29 wherein said normal force sensor element and said shear force sensor element are arranged in a vertically stacked disposition relative to one another.

* * * * *